US007239588B2

(12) United States Patent
Gotoh et al.

(10) Patent No.: US 7,239,588 B2
(45) Date of Patent: Jul. 3, 2007

(54) METHOD AND APPARATUS FOR DETECTING FOREIGN BODY ON OBJECT SURFACE, AND OPTICAL DISK APPARATUS

(75) Inventors: Yasuhiro Gotoh, Kadoma (JP); Seiji Nishiwaki, Kobe (JP); Yoshiaki Komma, Hirakata (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/516,023

(22) PCT Filed: May 30, 2003

(86) PCT No.: PCT/JP03/06805

§ 371 (c)(1), (2), (4) Date: May 19, 2005

(87) PCT Pub. No.: WO03/102563

PCT Pub. Date: Dec. 11, 2003

(65) Prior Publication Data

US 2005/0230647 A1 Oct. 20, 2005

(30) Foreign Application Priority Data

| May 30, 2002 | (JP) | ............................. 2002-156889 |
| Jul. 4, 2002 | (JP) | ............................. 2002-195488 |
| Aug. 5, 2002 | (JP) | ............................. 2002-227138 |
| Sep. 11, 2002 | (JP) | ............................. 2002-265101 |
| Mar. 19, 2003 | (JP) | ............................. 2003-075691 |

(51) Int. Cl.
*G01N 21/88* (2006.01)

(52) U.S. Cl. ................................. 369/53.2; 250/559.45

(58) Field of Classification Search ............ 250/559.45
See application file for complete search history.

(56) References Cited

U.S. PATENT DOCUMENTS 4,226,539 A * 10/1980 Nakagawa et al. ......... 356/445

FOREIGN PATENT DOCUMENTS

| JP | 62-14326 | 1/1987 |
| JP | 62-267651 | 11/1987 |
| JP | 62-297747 | 12/1987 |
| JP | 2-52242 | 2/1990 |
| JP | 2-163639 | 6/1990 |

(Continued)

*Primary Examiner*—Van Pham
(74) *Attorney, Agent, or Firm*—Wenderoth, Lind & Ponack, L.L.P.

(57) ABSTRACT

In an foreign body detection apparatus, an optical signal detection unit irradiates a light spot onto a surface of an object to be inspected while scanning the surface by employing the light spot in a predetermined direction, and receives a reflected beam from the surface of the inspected object to generate a photodetection signal corresponding to the light intensity of the reflected beam. A foreign body detection unit generates a foreign body detection signal appearing with respect to a leader and a trailer in the scanning direction of a foreign body adhering to the inspected object from the photodetection signal. The foreign body detection signal is obtained, for example, as a difference signal between the photodetection signal and a delayed photodetection signal with a predetermined delay time. A foreign body discrimination unit generates a foreign body discriminating signal indicating a region in which the foreign body is present from the foreign body detection signal.

39 Claims, 29 Drawing Sheets

FOREIGN PATENT DOCUMENTS

| | | |
|---|---|---|
| JP | 3-118453 | 5/1991 |
| JP | 4-221431 | 8/1992 |
| JP | 6-223384 | 8/1994 |
| JP | 10-79123 | 3/1998 |
| JP | 2001-256649 * | 9/2001 |

* cited by examiner

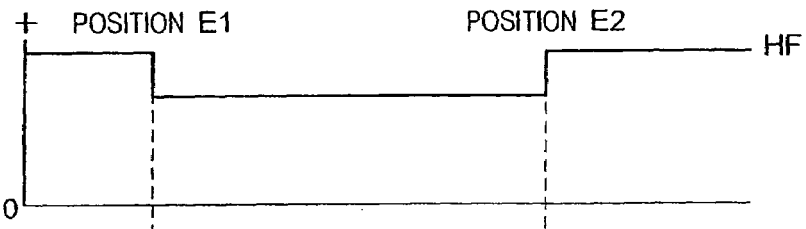
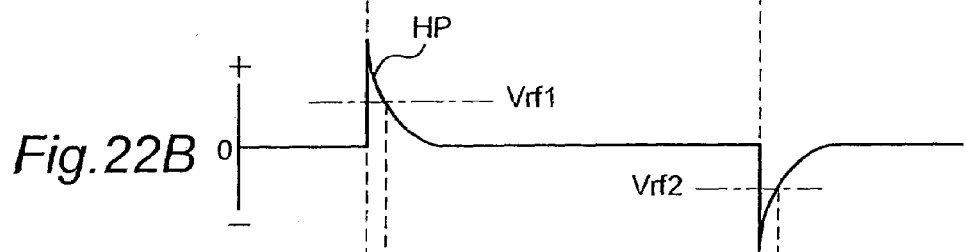
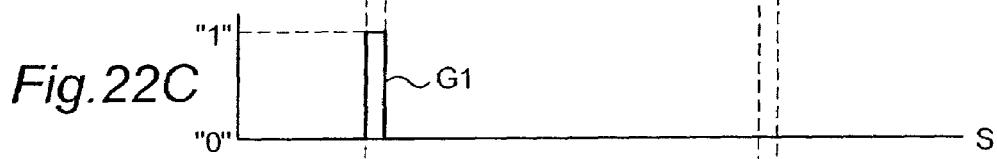
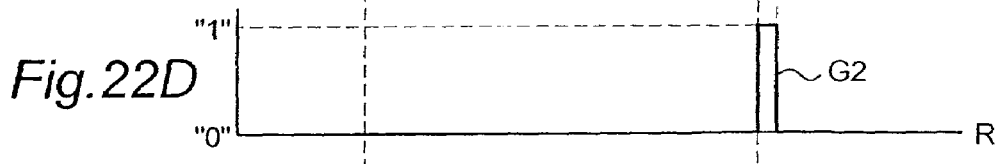
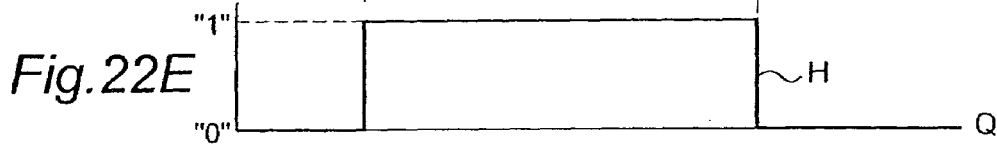

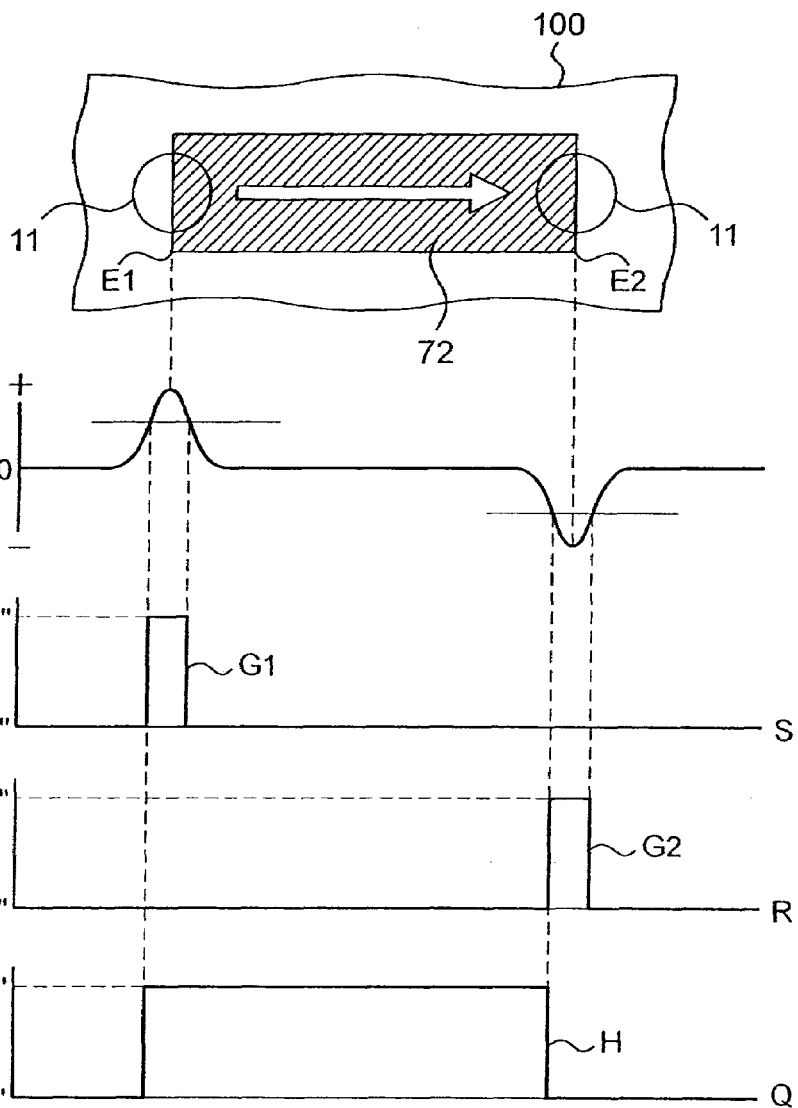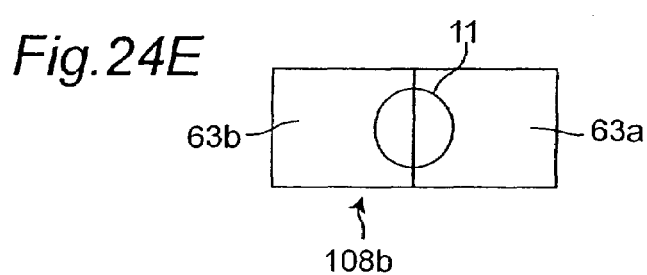

METHOD AND APPARATUS FOR DETECTING FOREIGN BODY ON OBJECT SURFACE, AND OPTICAL DISK APPARATUS

TECHNICAL FIELD

The present invention relates to a method and apparatus for detecting a foreign body such as a stain, dust, an oil film, a fingerprint, a scratch, or a defect adhering to or made on a surface of an object. In addition, the present invention relates to an optical disk apparatus which detects a foreign body on an optical disk surface by using the foreign body detection apparatus, and to various systems equipped with the optical disk apparatus.

BACKGROUND ART

In recent years, demands for an increase in information recording density on an optical disk recording/reproducing device (to be referred to as an "optical disk apparatus" unless otherwise noted hereinafter) using a phase change recording medium, a pigmentary change recording medium, a magneto-optical recording medium, an optical recording medium (to be referred to as an "optical disk" unless otherwise noted hereinafter) such as a read-only medium on which data is recorded in advance with concavo-convex or the like, an increase in density of pixels on an electronic imaging device such as a CCD (imaging element), a liquid crystal panel, or an organic EL panel, and an increase in miniaturization rate and integration density on a semiconductor integrated circuit have been high. From this background, efforts to miniaturize devices such as the optical disk apparatus, the electronic imaging device, and the semiconductor circuit to achieve higher integration are actively made.

However, with the advance of miniaturization of these devices, important technical problems have arisen for realizing integration higher than conventional integration by detecting and removing a foreign body such as a stain, dust, an oil film, or a scratch. In manufacturing or use of a product, a foreign body adhering to the device causes a decrease in manufacturing yield or product performance. For this reason, accurate detection of a foreign body has become important.

In particular, in the optical disk apparatus, a foreign body adhering to the surface of an optical disk is a disincentive factor of an increase in information recording density. More specifically, in the case where recording marks are reduced in size by using a short-wavelength light source such as a blue laser to increase a recording bit density, when even a foreign body which does not cause any problem on a compact disk adheres to an optical path of a light beam, the following problem arises. Therefore, the optical disk apparatus having a high information recording density cannot be easily put into practical use.

When a light beam is irradiated on a recording layer of an optical disk to form recording marks on the recording layer, the light beam is affected by light shielding, refraction, reflection, or the like depending on the optical characteristics of a foreign body adhering to the optical disk surface to cause the positions and sizes of the recording marks to vary. The influence of the variations increases as a light beam spot diameter and a recording mark length decrease. Thus, recording marks having high reliability and a high information recording density cannot be easily formed at high accuracy.

When a light beam is irradiated on the recording layer and the track layer of a phase change recording medium or a pigmentary change recording medium to read recording marks, the light beam is similarly affected by light shielding, refraction, reflection, or the like depending on the optical characteristics of a foreign body adhering to the surface of the optical disk, and thus, the recording marks and tracks cannot be correctly read. As the recording marks and tracking pitches are decreased in size, the influence of the foreign body increases. Therefore, recording marks having a high information recording density cannot be easily read at high accuracy.

The optical disk apparatus is expected to be developed in a new market as a large-capacity recording device with a small size, a light weight, and a low price. However, an optical disk apparatus with an increased capacity by increasing an information recording density has poor recording/reproducing reliability against a foreign body. Thus, when the optical disk apparatus is mounted on an apparatus or a system such as a computer apparatus, a computer system, a computer network system, a vehicle such as an automobile, a train, a ship, or an airplane, and an image complex apparatus such as an MFP (Multi-Function Product) which require recording/reproducing reliability, the reliabilities of the apparatuses and the systems are disadvantageously deteriorated.

In order to solve the above problem, an optical disk apparatus having a means for detecting a foreign body adhering to the surface of an optical disk is conventionally proposed.

FIG. 34 shows an example of such an optical disk apparatus, and is a schematic view of a stain detection device for an optical disk disclosed in a patent document JP6-223384A. A light radiated from a semiconductor laser light source 5 is converged on the surface of an optical disk 100 through an object lens 7, and the reflected light is received by a light-receiving element 53 having two divided regions A and B through a ¼ wavelength plate 51 and a polarized beam splitter 6. The light intensities of the lights received in the regions A and B are converted into voltages through I-V conversion circuits 54a and 54b, and the voltages in the regions A and B are added to each other by a sum signal reproducing circuit 55 to generate a sum signal voltage. On the other hand, the sum signal voltage calculated from the theoretical reflectance of the optical disk is set as a reference voltage of the optical disk which is free from stain. The sum signal voltage is compared with the reference voltage. When the sum signal voltage is lower than the reference signal voltage, a warning is given, or the operation is stopped.

SUMMARY OF THE INVENTION (Problems to be Solved by the Invention)

However, since the conventional foreign body detection apparatus directly compares the sum signal voltage with the reference voltage to detect a foreign body, a bias corresponding to (HF0−ΔHF) is generated, because HF0 is larger than ΔHF in which a decrease in the level of a portion to which a foreign body adheres and a level of a portion to which no foreign body adheres are represented by ΔHF and HF0, respectively. In a phase change recording medium, which is one of the fields to which the present invention is applied, considering another recording deterioration factors such as defocus, offtrack, a change in temperature of a medium or a device, and the like, the uppermost value and the lowermost value of a laser beam and irradiation energy for preferably recording data on an information layer in recording must be suppressed to 10% or less. In other words, preferable recording cannot be performed when the laser beam irradiation energy is larger or smaller than 10%, and upon reproducing an information signal, an error may occur to cause the reliability to be deteriorated. In particular, when a foreign body having a low reflectance adheres to the surface of an optical disk which is a recording medium, detection accuracy could be deteriorated unfortunately. Especially, the detection of a foreign body such as an oil film having a high optical transmittance becomes impossible disadvantageously. In addition, the detection accuracy of a foreign body is deteriorated in an ordinary measurement environment, and a control device with high-precision is required to improve the detection accuracy, thereby causing the device to be expensive. More specifically, when the foreign body is detected by the conventional foreign body detection apparatus, a difference in light intensity between a beam reflected by a portion to which the foreign body adheres and a beam reflected by a portion to which no foreign body adheres, i.e., a difference in sum signal voltage decreases, and the margin of the reference voltage also decreases. Therefore, in order to correctly detect such a foreign body, the sum signal voltage must be accurately stabilized. However, in an ordinary use environment, the sum signal voltages are varied by the aging or temperature changes of a light source, a photodetector, a signal processing circuit, and the like or dust adhering to an optical lens or the photodetector. Especially, when a foreign body has a high optical transmittance of not less than 90%, a difference in sum signal voltage becomes small and a reference voltage is fixed, and thus variation in sum signal voltage makes it impossible to detect the foreign body.

Therefore, the present invention has been made to solve the conventional problems. Accordingly, an object of the present invention is to provide a method and apparatus which are capable of detecting a foreign body with a reflectance which is slightly different from a reflectance of the medium or a transparent foreign body at high accuracy, and providing a large margin for a variation of a photodetector. It is another object of the invention to provide a foreign body detection apparatus which is capable of detecting a foreign body at a high accuracy and a low cost even in an ordinary measurement environment. It is still another object to provide an optical disk apparatus and a system equipped with the optical disk apparatus which can achieve recording/reproducing high-density information and provide high reliability against a foreign body.

(Method of Solving the Problems)

A method of detecting a foreign body on a surface of an object according to the present invention includes the steps of irradiating a light spot onto a surface of an object to be inspected while scanning the surface by irradiating the light spot in a predetermined direction, receiving a reflected beam from the surface of the inspected object to generate a photodetection signal corresponding to the light intensity of the reflected beam, generating a foreign body detection signal appearing with respect to a leader and a trailer in the scanning direction of the foreign body adhering to the inspected object, based on the photodetection signal, and generating a foreign body discriminating signal indicating a region in which the foreign body is present based on the foreign body detection signal.

In the detecting method, the step of generating a foreign body detection signal may include the steps of generating a delay signal obtained by delaying the photodetection signal by a predetermined period of time and performing subtraction between the delay signal and the photodetection signal to generate a difference signal. In this case, the step of generating a foreign body discrimination signal generates the foreign body discrimination signal based on the difference signal.

Alternatively, in the detecting method, the step of generating a foreign body detection signal may include the steps of generating a first delay signal obtained by delaying the photodetection signal by a first delay time, generating a second delay signal obtained by delaying the photodetection signal by a second delay time, and performing subtraction between the first and second delay signals to generate a difference signal. Then, the step of generating a foreign body discrimination signal generates the foreign body discrimination signal based on the difference signal.

Alternatively, in the detecting method, the step of generating a foreign body detection signal may include the step of causing the photodetection signal to pass through a band-pass filter to generate a band-pass signal. Then, the step of generating a foreign body discrimination signal generates the foreign body discrimination signal based on the band-pass signal.

Alternatively, in the detecting method, the step of generating a foreign body detection signal may include the steps of causing the photodetection signal to pass through a low-pass filter to generate a low-band signal and performing subtraction between the photodetection signal and the low-band signal to generate a difference signal. Then, the step of generating a foreign body discrimination signal generates the foreign body discrimination signal based on the difference signal.

Alternatively, in the detecting method, the step of generating a foreign body detection signal may include the steps of causing the photodetection signal to pass through a first low-pass filter to generate a first low-band signal, causing the photodetection signal to pass through a second low-pass filter having a passing band characteristic different from that of the first low-pass filter to generate a second low-band signal, and performing subtraction between the first low-band signal and the second low-band signal to generate a difference signal. Then, the step of generating a foreign body discrimination signal generates the foreign body discrimination signal based on the difference signal.

Alternatively, in the detecting method, the step of generating a foreign body detection signal may include the steps of causing the photodetection signal to pass through the first low-pass filter to generate a first low-band signal, causing the first low-band signal to pass through a second low-pass filter having a frequency characteristic different from that of the first low-pass filter to generate a second low-band signal, and performing subtraction between the first low-band signal and the second low-band signal to generate a difference signal. Then, the step of generating a foreign body discrimination signal generates the foreign body discrimination signal based on the difference signal.

Alternatively, in the detecting method, the step of generating a foreign body detection signal may include the step of causing the photodetection signal to pass through a high-pass filter to generate a high-band signal. Then, the step of generating a foreign body discrimination signal generates the foreign body discrimination signal based on the high-band signal.

An apparatus for detecting a foreign body on an object surface according to the present invention includes an irradiation unit that irradiates a light spot onto a surface of an object to be inspected while scanning the surface by irradiating the light spot in a predetermined direction, an optical signal detection unit that receives a reflected beam from the surface of the inspected object to generate a photodetection signal corresponding to the light intensity of the reflected beam, a foreign body detection unit that generates a foreign body detection signal appearing with respect to a leader and a trailer in the scanning direction of a foreign body adhering to the inspected object, based on the photodetection signal, and a foreign body discrimination unit that generates a foreign body discriminating signal indicating a region in which the foreign body is present based on the foreign body detection signal.

The foreign body detection unit may include a delay unit that generates a delay signal obtained by delaying the photodetection signal by a predetermined time, and a subtraction unit that generates a difference signal by performing subtraction between the delay signal and the photodetection signal. Then, the foreign body discrimination unit generates the foreign body discrimination signal based on the difference signal.

Alternatively, the foreign body detection unit may include a first delay unit that generates a first delay signal obtained by delaying the photodetection signal by a first delay time, a second delay unit that generates a second delay signal obtained by delaying the photodetection signal by a second delay time, and a subtraction unit that performs subtraction between the first delay signal and the second delay signal to generate a difference signal. Then, the foreign body discrimination unit generates the foreign body discrimination signal based on the difference signal.

Alternatively, the foreign body detection unit may include a band-pass filter that causes the photodetection signal to pass therethrough to generate a band-pass signal. Then, the foreign body discrimination unit generates the foreign body discrimination signal based on the band-pass signal.

Alternatively, the foreign body detection unit may include a low-pass filter that causes the photodetection signal to pass therethrough to generate a low-band signal and a subtraction unit that performs subtraction between the photodetection signal, and the low-band signal to generate a difference signal. Then, the foreign body discrimination unit generates the foreign body discrimination signal based on the difference signal.

Alternatively, the foreign body detection unit may include a first low-pass filter that causes the photodetection signal to pass therethrough to generate a first low-band signal, a second low-pass filter that has a passing band characteristic different from that of the first low-pass filter and causes the photodetection signal to pass therethrough to generate a second low-band signal, and a subtraction unit that performs subtraction between the first low-band signal and the second low-band signal to generate a difference signal. Then, the foreign body discrimination unit generates the foreign body discrimination signal based on the difference signal.

Alternatively, the foreign body detection unit may include a first low-pass filter that causes low-band components of the photodetection signal to pass therethrough to generate a first low-band signal, a second low-pass filter that has a passing band characteristic different from that of the first low-pass filter and causes the first low-band signal to pass therethrough to generate a second low-band signal, and a subtraction unit that performs subtracting between the first low-band signal and the second low-band signal to generate a difference signal. Then, the foreign body discrimination unit generates the foreign body discrimination signal based on the difference signal.

Alternatively, the foreign body detection unit may include a high-pass filter that causes the photodetection signal to pass therethrough to generate a high-band signal. Then, the foreign body discrimination unit generates the foreign body discrimination signal based on the high-band signal.

An optical disk apparatus according to the invention is an apparatus for irradiating a laser beam on an optical disk to record or reproduce information, and includes the above-described foreign body detection apparatus that detects a foreign body adhering to the surface of an optical disk which is an object to be inspected.

It is noted that the following applications are allowed by using the above optical disk apparatus:

a computer system including a computer device having a microcomputer, a memory, and an external transmission path, a communication device, an output device, and the optical disk apparatus described above;

a computer network system including at least one computer device having a microcomputer, a memory, and an external transmission path, a communication device for connecting the computer device through communication means, an input device, and at least one of the optical disk apparatuses described above;

a transportation means such as an automobile, a ship, or an airplane including power generating means, power transmission means, and the optical disk apparatus;

an image complex apparatus which is equipped with the optical disk apparatus, including an image forming apparatus, an image reading apparatus, a microcomputer, a memory and an external transmission path; and a cinema system including a projection screen, the optical disk apparatus described above, a control unit that generates a video/audio signal from a signal reproduced from the optical disk apparatus, a projection means for projecting a video image on the screen based on a video/audio signal, and sound output means for outputting sound based on the video/audio signal.

The cinema system may include two or more optical disk apparatuses. In this case, when a foreign body is detected on the optical disk apparatus in reproduction, the control unit controls the optical disk apparatuses to stop the reproducing operation performed by the optical disk apparatus in reproduction and to start the reproducing operation performed by the other optical disk apparatus.

BRIEF DESCRIPTION OF THE DRAWINGS

FIGS. 22A to 22E are charts showing waveforms of signals obtained in the detection of a foreign body in the foreign body detection apparatus having the seventh configuration.

FIGS. 24A to 24D are charts showing signal waveforms of signals obtained in the detection of a foreign body in the foreign body detection apparatus having the eighth configuration.

FIG. 24E is a diagram showing the relationship between a photodetector 108b and a light spot 11.

DETAILED DESCRIPTION OF THE INVENTION

Preferred embodiments of a foreign body detection apparatus according to the present invention and various apparatuses using the same will be described below with reference to the accompanying drawings.

First Embodiment

Figure 1:
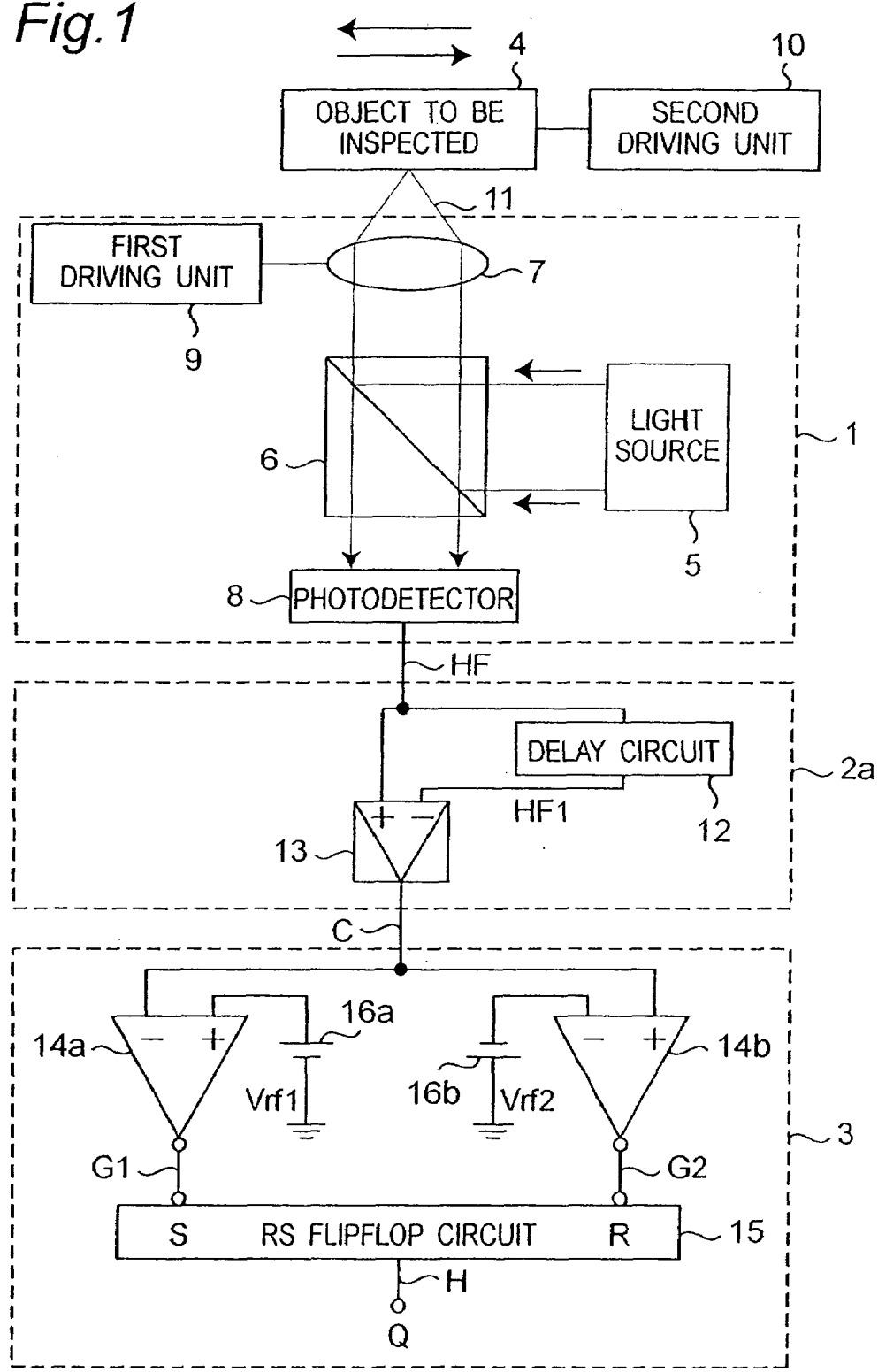
FIG. 1 is a block diagram showing the first configuration of a foreign body detection apparatus according to the present invention.

FIG. 1 is a block diagram showing the first configuration of a foreign body detection apparatus according to the present invention. The foreign body detection apparatus includes a photodetection signal generation unit 1, a foreign body detection signal generation unit 2a, a foreign body discrimination signal generation unit 3, and a second driving unit 10 for horizontally moving an object 4 to be inspected.

The photodetection signal generation unit 1 is a unit which detects a beam reflected by the surface of the object 4 to be inspected to generate a photodetection signal HF, and includes a light source 5, a beam splitter 6, a convergence means 7 such as an object lens, a photodetector 8, and a first driving unit 9 for moving a focal point of the convergence means 7.

As the light source 5, any well-known light source such as an incandescent lamp, a halogen lamp, a semiconductor laser, or a gas laser can be applied. Of these light sources, a light source such as a laser beam source having coherence is preferably used because the light source can detect a foreign body at high accuracy.

Figure 2:
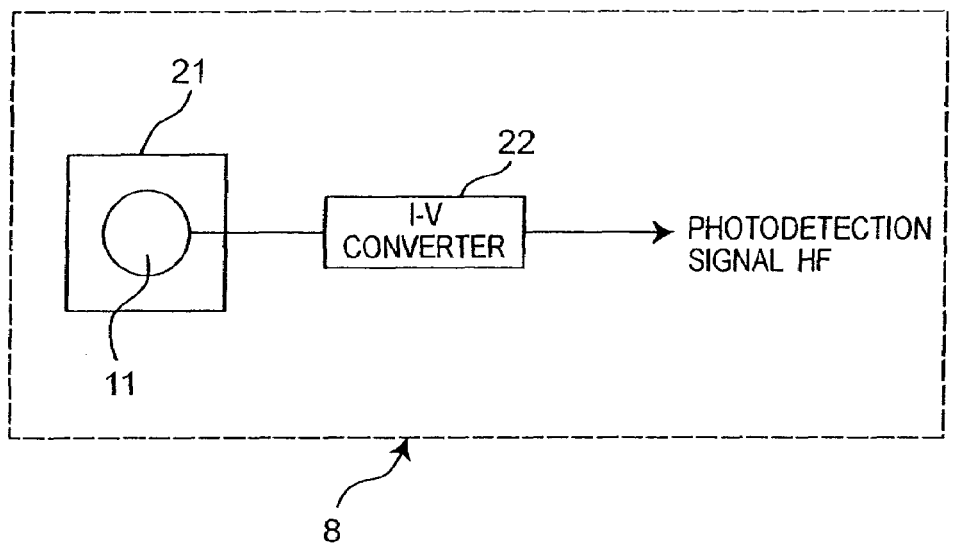
FIG. 2 is a diagram showing a configuration of a photodetector.

The photodetector 8, as shown in FIG. 2, includes a photoelectric conversion element 21 for converting the light intensity of a received beam into a current and an I-V converter 22 for converting the current into a voltage. As the photoelectric conversion element 21, any well-known element such as a photodiode or a CCD can be applied. The operation of the photodetection signal generation unit 1 having the above configuration is described below.

The first driving unit 9 is driven to move the convergence means 7 such that a beam emitted from the light source is converged on the surface of the object 4 to be inspected. In this state, a beam emitted from the light source 5 is reflected by the beam splitter 6 and converged on the surface of the object 4 to be inspected by the convergence means 7. The beam reflected from the surface of the object 4 to be inspected passes through the beam splitter 6, and is received by the photodetector 8 and converted into a voltage depending on the light intensity of the received beam, thus to be output from the photodetector 8 as a photodetection signal HF.

The diameter and shape of a light spot 11 obtained by converging the beam on the surface of the object 4 to be inspected are determined by appropriately selecting an optical system depending on targets such as the type and size of an object to be inspected or the type and size of a foreign body to be detected.

The diameter of the light spot is preferably in a range of Φ1 µm to Φ5 mm but it does not always fall within this range. It is understood that the light spot diameter is appropriately selected depending on the size of a foreign body or a particular purpose. The light spot diameter can be easily changed by the following ordinary means including: 1) moving the focal point of the object lens; and 2) replacing the optical system with an optical system from which a desired light spot diameter can be obtained. In particular, when a laser beam source is used as the light source 5, it is a preferable that the optical system is arranged such that the surface of the object 4 to be inspected is located at approximately a focal point of the object lens because the peripheral boundary of a foreign body can be detected by a simple optical configuration. Especially, in an optical disk apparatus (to be described later), with the above configuration, the optical system can be advantageously used without any changes.

The light spot shape may be preferably changed into a circle, an ellipse, a rectangle, or the like depending on a target. In order to change the light spot diameter, a mask punched out to have a desired shape may be inserted into an optical path, or a cylindrical lens may be used. The foreign body detection signal generation unit 2a includes a delay circuit 12 for generating a delay signal HF1 obtained by delaying the photodetection signal HF output from the photodetector 8 by a delay time T, and a subtractor 13 for subtracting the photodetection signal HF1 from the delay signal HF to generate a difference signal C. The gain of the subtractor 13 is represented by n. The value n may be 1 or more or less than 1, and is preferably set at a value that is suitable for a circuit design.

The foreign body discrimination signal generation unit 3 is a unit for discriminating a foreign body based on the difference signal C output from the subtractor 13, and includes comparators 14a and 14b and an RS flip-flop circuit 15.

Reference voltage generators 16a and 16b are connected to the comparators 14a and 14b, respectively. Reference voltages Vrf1 and Vrf2 respectively generated by the reference voltage generators 16a and 16b have opposite polarities from each other and approximately equal absolute values. It is preferable to reset the reference voltage values every measurement because it provides a high detection accuracy of a foreign body.

The operation of the foreign body discrimination signal generation unit 3 having the above configuration will be described below.

When the difference signal C output from the foreign body detection signal generation unit 2a is input to the comparators 14a and 14b, the voltage of the difference signal C is compared with the reference voltages Vrf1 and Vrf2 output from the reference voltage generators 16a and 16b, respectively. When reference voltage Vrf1<0 and reference voltage Vrf2>0 are satisfied, i.e., when (reference voltage Vrf1−voltage of difference signal C)<0 or (reference voltage Vrf2−voltage of difference signal C)>0 is satisfied at the peripheral boundary of the foreign body (the leader and trailer of the foreign body), digital signals "1" are output from the comparators 14a and 14b, respectively. At a region except for the peripheral boundary of the foreign body, reference voltage Vrf1<voltage of difference signal C<reference voltage Vrf2, and thus digital signals "0" are output from the comparators 14a and 14b, respectively. Therefore, detection of the output signals from the comparators 14a and 14b enables the presence/absence of the foreign body to be discriminated. When this output signal is input to the RS flipflop circuit 15, an area between the leader of the periphery of the foreign body and the trailer of the periphery is converted into a digital signal of "1". For this reason, it is preferable in that the region of the foreign body can be easily discriminated.

A scanning method of the light spot 11 irradiated on the object 4 to be inspected will be described below.

Figure 3:
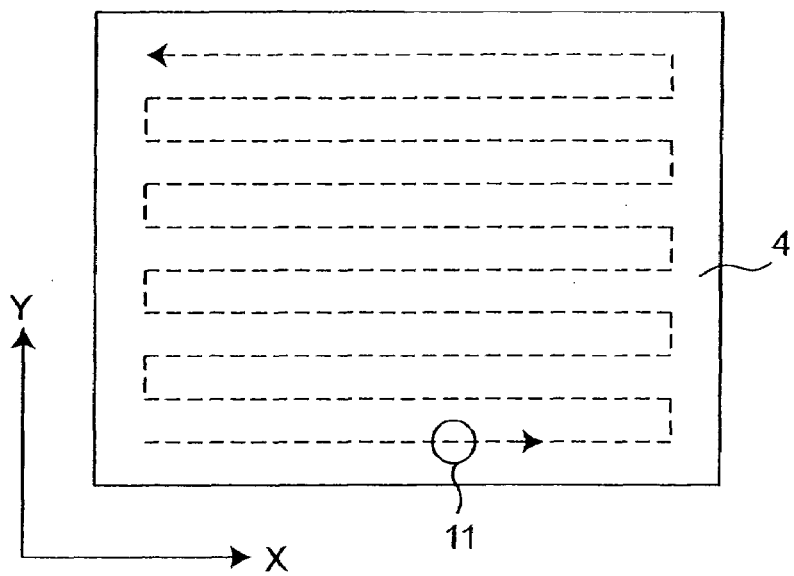
FIG. 3 is a diagram showing an example of a scanning method of a light spot.

FIG. 3 shows a scanning method especially suitable for a case in which the object 4 to be inspected is rectangular. The relative positions of the object 4 to be inspected and the photodetection signal generation unit 1 are parallelly moved in an X direction and a Y direction by the second driving unit 10 to cause the light spot 11 to scan the object 4 to be inspected in a direction indicated by a broken line. When a laser beam source is used as a light source, the following method may be used. That is, the laser beam is caused by a polygon mirror to scan the object 4 to be inspected in the X direction while the object 4 to be inspected is moved in the Y direction.

Figure 4:
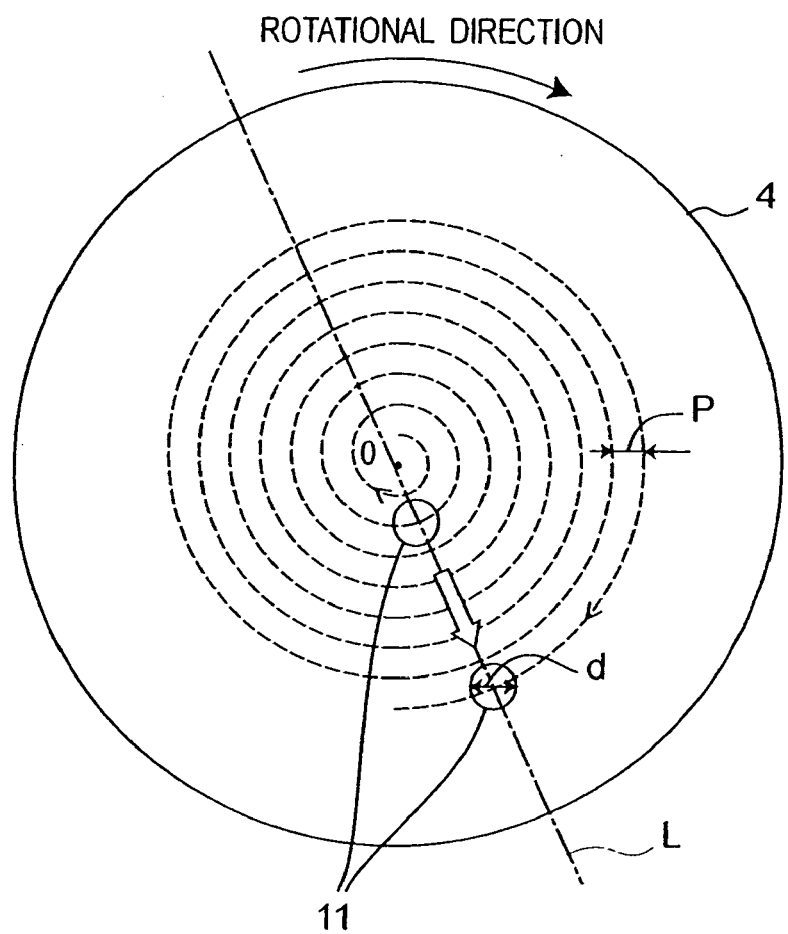
FIG. 4 is a diagram showing another example of the scanning method of the light spot.

FIG. 4 explains a scanning method which is especially suitable for a case in which the object 4 to be inspected has a circular shape like an optical disk. The light spot 11 is moved in a direction of an arrow along a center line L ("O" in FIG. 4 indicates the center point of the object to be inspected) to cause the light spot 11 to scan the object 4 to be inspected such that the light spot 11 follows a spiral track.

Figure 5:
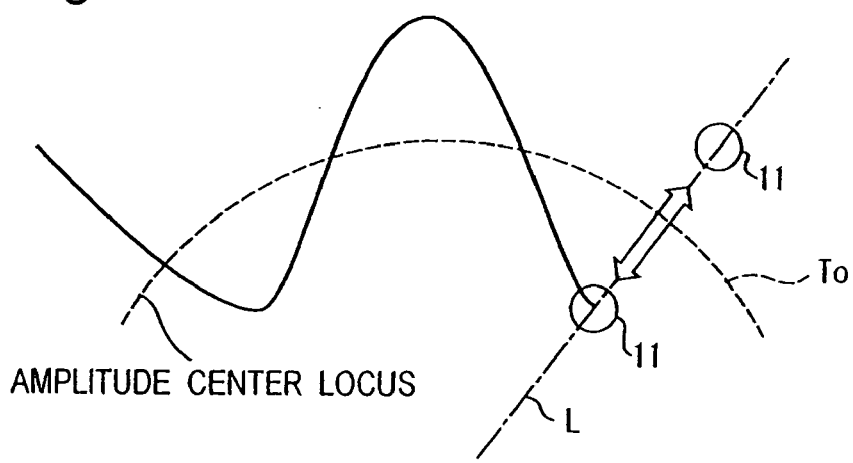
FIG. 5 is a diagram showing still another example of the scanning method of the light spot.

FIG. 5 is a diagram for explaining another example of a scanning method which is suitable for a case in which the object 4 to be inspected has a circular shape. The light spot 11 is oscillated at a predetermined amplitude while rotating the object 4 to be inspected, and at the same time, the light spot 11 is moved along the center line L of the object 4 to be inspected and caused to scan the object 4 to be inspected such that a center locus To of the amplitude is spiral. This method is preferable because the measuring time can be shortened.

Figure 6:
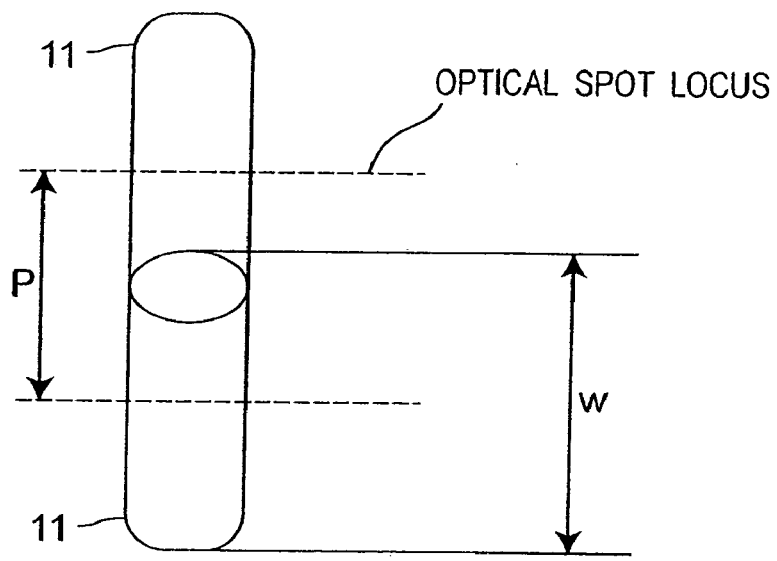
FIG. 6 is a diagram for explaining the relationship between the width of the light spot and a scanning pitch.

FIG. 6 is an enlarged diagram showing the relationship between a scanning pitch P and a light spot width W of the light spot 11 described in FIGS. 3 to 5. It is preferable to make the width W of the light spot larger than the scanning pitch P (P<W) to cause tracks of the light spot 11 to partially overlap because the light spot 11 can entirely scan the region to be inspected. When the light spot 11 has a circular shape, it is preferable that the scanning pitch P is equal to or less than a diameter d of the light spot 11 for the same reason as described above. In order to conveniently and simply detect the presence/absence of a foreign body, the scanning pitch P of the light spot 11 may be made larger than a light spot width W.

A method of detecting a foreign body by the foreign body detection apparatus will be described below with reference to FIGS. 7 and 8A to 8F.

Figure 7:
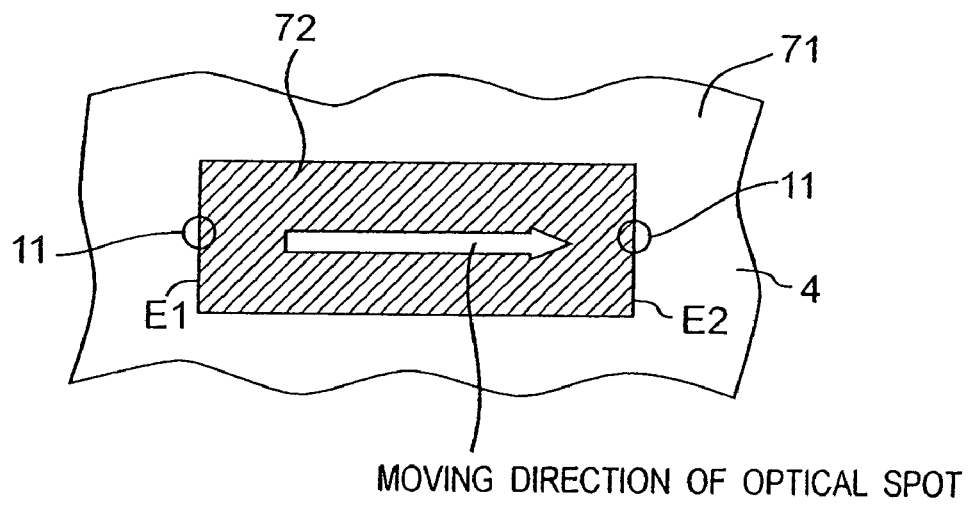
FIG. 7 is a diagram for explaining a method of detecting a foreign body by using the foreign body detection apparatus.

FIGS. 8A to 8F are charts showing, when an object 71 to which a foreign body 72 having a surface reflectance lower than that of the surface of the object 71 adheres is used as the object 4 to be inspected, as shown in FIG. 7, signals obtained near the foreign body 72 which are output from the photodetection signal generation unit 1, the foreign body detection signal generation unit 2a, and the foreign body discrimination signal generation unit 3.

The light spot 11 is irradiated on the object 4 (71) to be inspected while scanning the object 4 (71) to be inspected in the direction of an arrow, and a reflected beam from the object 4 (71) to be inspected is received by the photodetector 8. At this time, the light intensity of the reflected beam from the foreign body 72 is lower than the light intensity of the reflected beam from the surface of the object 71. For this reason, as shown in FIG. 8A, a photodetection signal HF having a waveform in which the signal level of the part of the foreign body 72 (between a peripheral portion E1 and a peripheral portion E2) is lower than the signal level of the surface of the object 71 is output from the photodetector 8.

Figure 8:
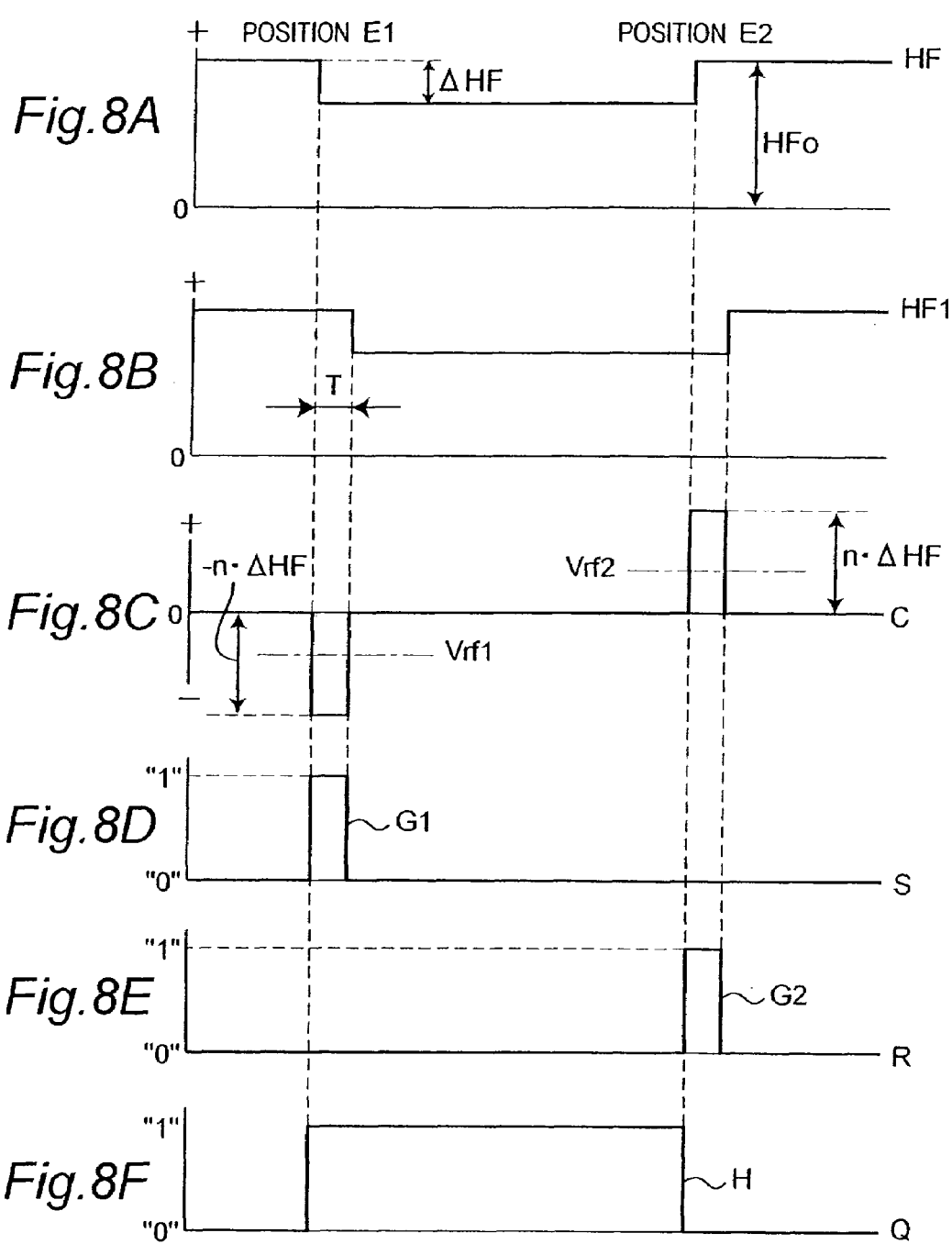
FIGS. 8A to 8F are charts showing waveforms of signals obtained in the detection of a foreign body in the foreign body detection apparatus having the first configuration.

When the photodetection signal HF output from the photodetector 8 is input to the delay circuit 12, the waveform of the delay signal HF1 obtained by delaying the photodetection signal HF by time T is output from the delay circuit 12 as shown in FIG. 8B.

The photodetection signal HF output from the photodetector 8 and the delay signal HF1 output from the delay circuit 12 are input to the subtractor 13 to subtract the photodetection signal HF from the delay signal HF1 (HF−HF1). The waveform of the difference signal C as shown in FIG. 8C is output from the subtractor 13. More specifically, a negative-pulse waveform G1 is output because HF<HF1 is satisfied at the peripheral portion E1 of the foreign body, the waveform having 0 level is output because HF=HF1 is satisfied at a position between the peripheral portion E1 and the peripheral portion E2, and a positive-pulse waveform G2 is output because HF>HF1 is satisfied at the peripheral portion E2 of the foreign body.

The difference signal C output from the subtractor 13 is input to the comparators 14a and 14b to compare the reference voltages Vrf1 and Vrf2 with the difference signal C in voltage. The following fact was found out by an experiment. That is, when a decrease in level of the photodetection signal HF between the peripheral portion E1 and the peripheral portion E2 which are portions to which the foreign body adheres is represented by $\Delta HF$, the absolute values of the reference voltages Vrf1 and Vrf2 are about 30% to 70% of $n*\Delta HF$ to make it possible to detect the foreign body without an error. Therefore, the absolute value is preferably fixed to 30% to 70% of $n*\Delta HF$. In addition, the following fact was found out. As an experiment result obtained by using an object to be inspected to which various stains, oil films, and finger prints adhere or in which scratches and defects are formed, the foreign body can be maximally stably detected when the absolute values of the reference voltages Vrf1 and Vrf2 are 50% of $n*\Delta HF$. Therefore, it is most preferable to set the absolute values at about 50% of $n*\Delta HF$. A digital signal of "1" is output from the comparator 14a when the voltage of the difference signal C is lower than reference voltage Vrf1, and a digital signal of "0" is output from the comparator 14a when the voltage of the difference signal C is higher than the reference voltage Vrf1. Therefore, as shown in FIG. 8D, a signal waveform G1 of "1" is output from the comparator 14a at only the peripheral portion E1, and a signal waveform G1 of "0" is output from the comparator 14a at other portions. A digital signal of "1" is output from the comparator 14b when the voltage of the difference signal C is higher than the reference voltage Vrf2 as shown in FIG. 8E, and a digital signal of "0" is output from the comparator 14b when the voltage of the difference signal C is lower than the reference voltage Vrf2. Therefore, as shown in FIG. 8E, a signal waveform G2 of "1" is output from the comparator 14b at only the peripheral portion E2, and a signal waveform G1 of "0" is output from the comparator 14b at other portions. The signals G1 and G2 are signals indicating ends of the foreign body. Thus, the detection of the signals G1 and G2 makes it possible to determine that the foreign body is present between the portions. As described above, when the above processes are performed, the foreign body can be detected. However, for discriminating the position or size of a foreign body, it is preferable that a portion having a foreign body and a portion being free from a foreign body are converted into digital signals "1" and "0", respectively, because digital signals can be conveniently processed. Therefore, the signals G1 and G2 are input to the RS flip-flop circuit 15, and a signal H having a waveform in which a portion between the peripheral portions E1 and E2 is converted into "1" is generated as shown in FIG. 8F.

As described above, according to the foreign body detection apparatus of this embodiment, with respect to a decrease in level $\Delta HF$ of the signal HF caused by adhesion of a foreign body, $-n*\Delta HF$ and $+n*\Delta HF$ are generated as the difference signal C. The bias level $(HF0-\Delta HF)$ is removed from the difference signal C by the subtractor, and thus, the detection accuracy of a foreign body having a low reflectance or a transparent foreign body, and the range of a detectable foreign body can be advantageously increased. In addition, since a margin is increased against a variation of a light intensity of a beam received by the photodetection unit, a foreign body can be correctly detected even in an ordinary measurement environment. Furthermore, applying the foreign body detection apparatus to an optical disk apparatus, the reliability against a foreign body is improved in the optical disk apparatus and the optical disk apparatus built-in system, resulting in recording or reproducing high-density information with a laser beam having a short wavelength. These advantages can also be obtained in a foreign body detection apparatus which will be described in the following embodiments.

Second Embodiment

Figure 9:
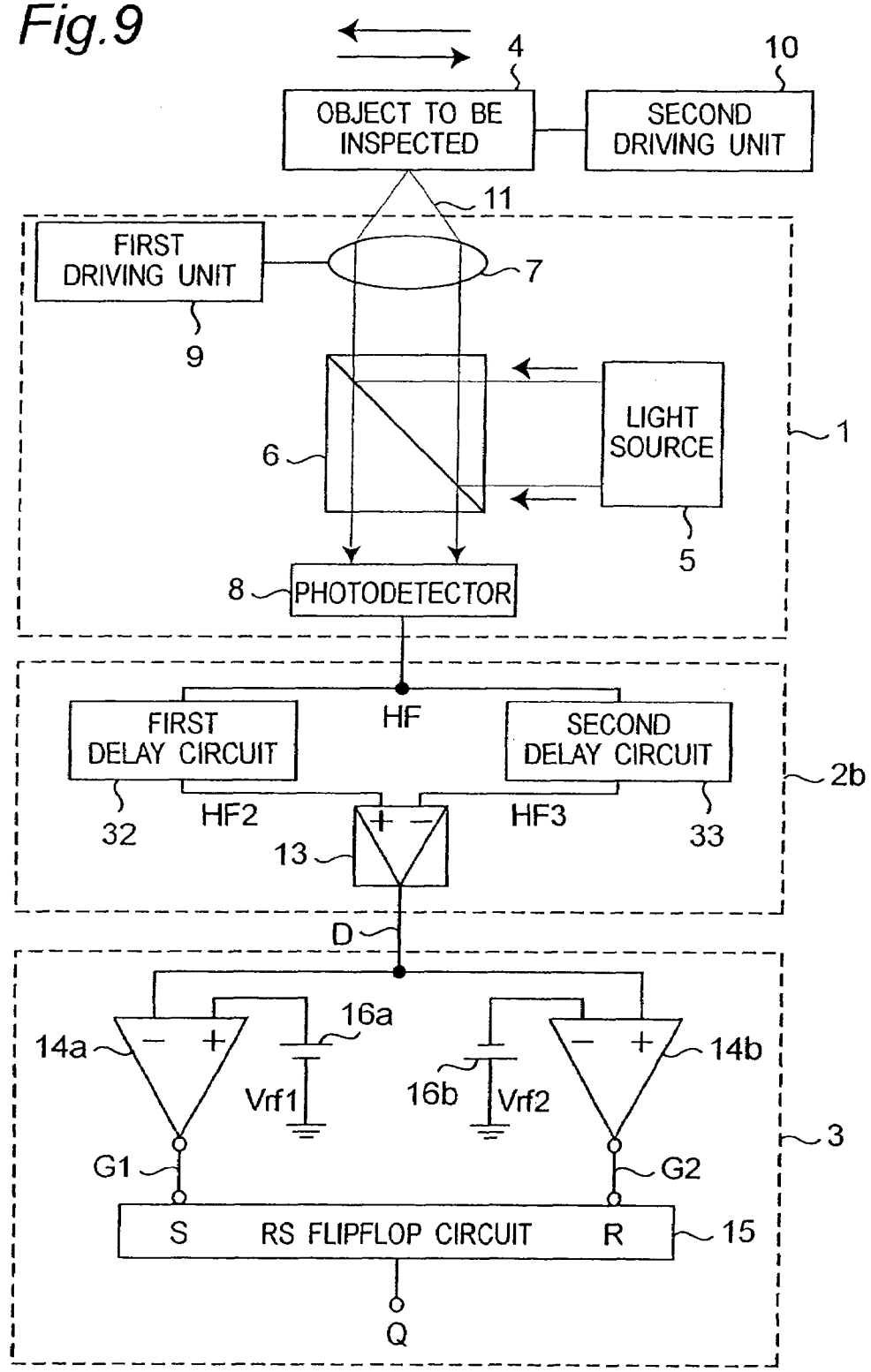
FIG. 9 is a block diagram showing the second configuration of the foreign body detection apparatus according to the present invention.

FIG. 9 is a block diagram showing the second configuration of a foreign body detection apparatus according to the present invention. The detection apparatus includes a photodetection signal generation unit 1, a foreign body detection signal generation unit 2b, a foreign body discrimination signal generation unit 3, and a second driving unit 10 for horizontally moving the object 4 to be inspected. The configurations and operations of the photodetection signal generation unit 1 and the foreign body discrimination signal generation unit 3 are the same as those described in FIG. 1.

The foreign body detection signal generation unit 2b includes a first delay circuit 32 and a second delay circuit 33 for delaying a photodetection signal HF output from the photodetector 8, and a subtractor 13. The subtractor 13 subtracts a delay signal HF3 output from the second delay circuit 33 from a delay signal HF2 output from the first delay circuit 32 to generate a difference signal D.

A foreign body detection method achieved by the foreign body detection apparatus shown in FIG. 9 will be described below with reference to FIGS. 10A to 10G.

FIGS. 10A to 10G are charts showing, in which the same inspected object 4 as described in conjunction with FIG. 7 is used, signals obtained near a foreign body 72 which are output from the photodetection signal generation unit 1, the foreign body detection signal generation unit 2b, and the foreign body discrimination signal generation unit 3.

Figure 10:
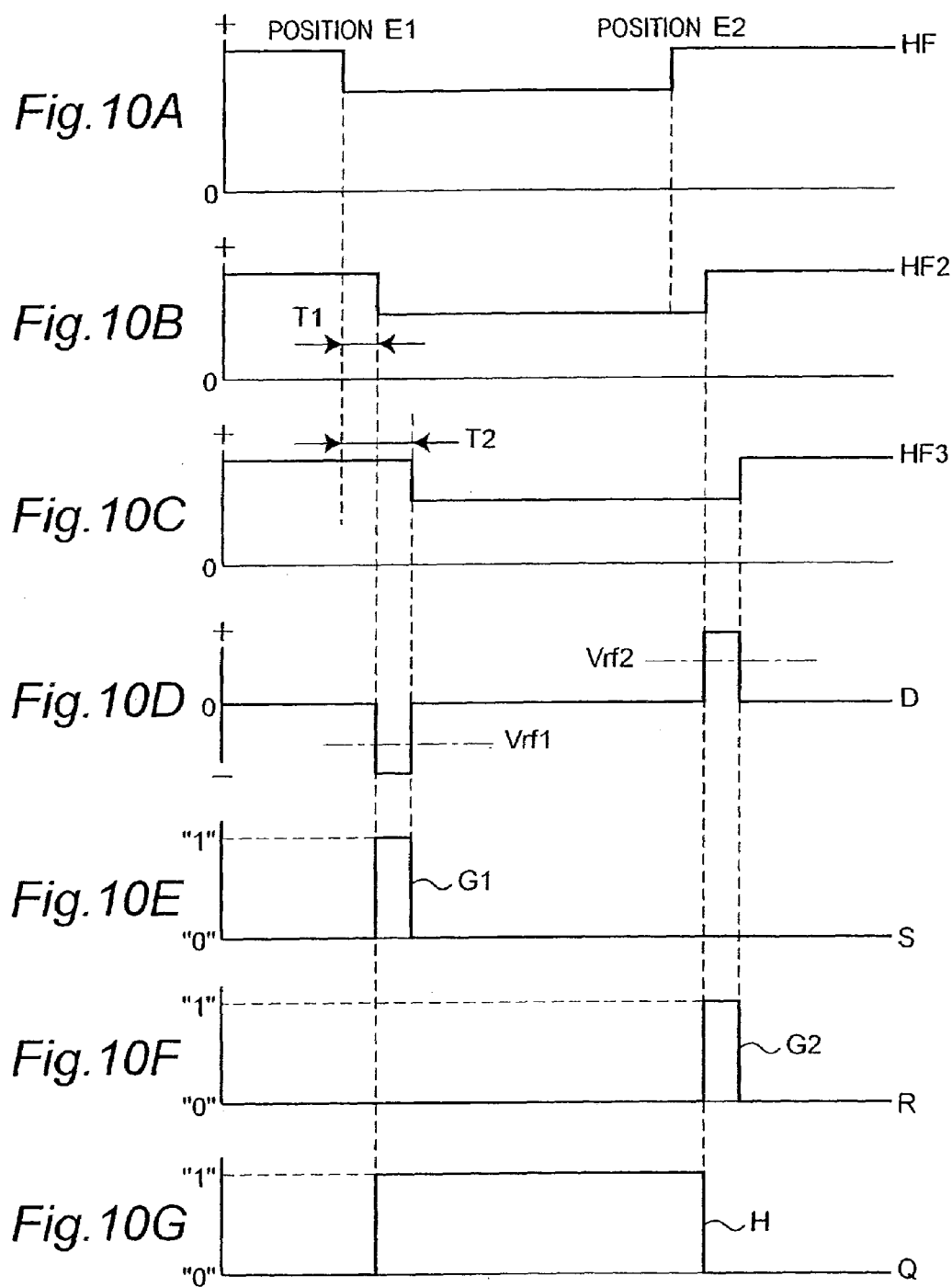
FIGS. 10A to 10G are charts showing waveforms of signals obtained in the detection of a foreign body in the foreign body detection apparatus having the second configuration.

By the same method as described in the first embodiment, a reflected beam from the object 4 to be inspected is received by the photodetector 8. A photodetection signal HF shown in FIG. 10A is output from the photodetector 8.

The photodetection signal HF output from the photodetector 8 is input to the first delay circuit 32 and the second delay circuit 33. At this time, from the first delay circuit 32, as shown in FIG. 10B, a delay signal HF2 obtained by delaying the photodetection signal HF by a period of time T1 is output. From the second delay circuit 33, as shown in FIG. 10C, a delay signal HF3 obtained by delaying the photodetection signal HF by a period of time T2 is output.

The delay signal HF2 and the delay signal HF3 are input to the subtractor 13 to subtract the delay signal HF3 from the delay signal HF2. At this time, a difference signal waveform D shown in FIG. 10D is output from the subtractor 13. More specifically, HF2 is lower than HF3 at a peripheral portion E1 of the foreign body, and a negative-pulse waveform is output. HF2 is equal to HF3 between the peripheral portion E1 and the peripheral portion E2, and a waveform of 0 level is output. HF2 is greater than HF3 at the peripheral portion E2 of the foreign body, and a positive-pulse waveform is output.

The difference signal output from the subtractor 13 is input to comparators 14a and 14b. The comparator 14a outputs a signal G1 which is "1" at only the peripheral portion E1 and "0" at the other portions as shown in FIG. 10E. The comparator 14b outputs a signal G2 which is "1" at only the peripheral portion E2 and "0" at the other portions as shown in FIG. 10F. Therefore, it is determined that the foreign body exists in the area corresponding to portion between the signals G1 and G2, by detecting the signals G1 and G2.

The above processes achieves detection of the foreign body sufficiently. In addition, the signals G1 and G2 are input to the RS flipflop circuit 15 to generate a signal H having a waveform in which a portion between the peripheral portions E1 and E2 is converted into "1", as shown in FIG. 10G. Hence, the region of the foreign body can be discriminated more easily.

The second configuration is suitable for digital signal processing. In recent years, in progress of digitization of various devices, a reduction in cost and a reduction in size can be realized by reducing the number of electronic parts. Therefore, the second configuration provides an excellent advantage.

Third Embodiment

Figure 11:
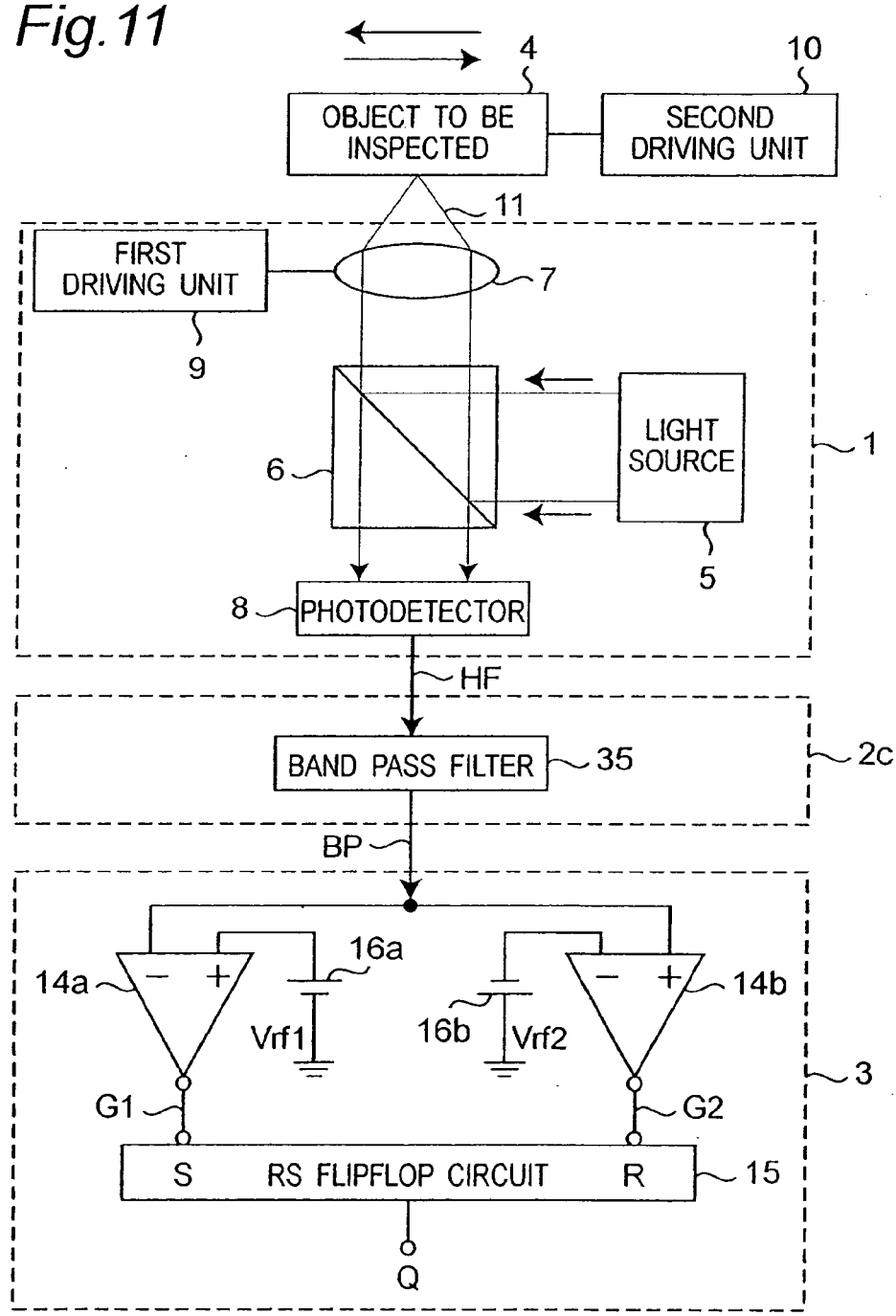
FIG. 11 is a block diagram showing the third configuration of the foreign body detection apparatus according to the present invention.

FIG. 11 is a block diagram showing the third configuration of the foreign body detection apparatus according to the present invention. The foreign body detection apparatus includes a photodetection signal generation unit 1, a foreign body detection signal generation unit 2c, and a foreign body discrimination signal generation unit 3. The configurations and operations of the photodetection signal generation unit 1 and the foreign body discrimination signal generation unit 3 are the same as those shown in FIG. 1.

Figure 12:
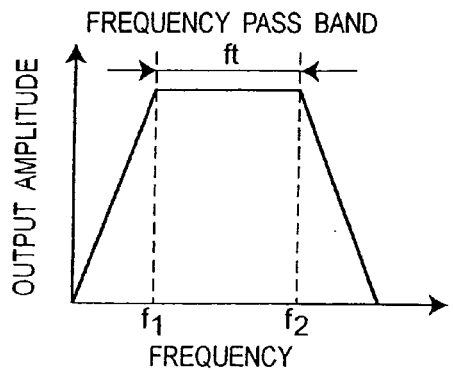
FIG. 12 is a graph showing a passing band characteristic of a band-pass filter of the foreign body detection apparatus having the third configuration.

The foreign body detection signal generation unit 2c includes a band-pass filter 35 which removes unnecessary band components of a photodetection signal HF output from the photodetector 8 to generate a band-pass signal. The band-pass filter 35 has a band-pass characteristic to pass only a predetermined frequency band ft as shown in FIG. 12.

The foreign body discrimination signal generation unit 3 is different from that of the first embodiment in that a band-pass signal BP output from the band-pass filter 35 is inputted thereto, while the subsequent basic operations are the same as those in the first embodiment.

A foreign body detection method achieved by the foreign body detection apparatus according to this embodiment will be described below with reference to FIGS. 13A to 13E.

FIGS. 13A to 13E are charts showing signals output from the photodetection signal generation unit 1, the foreign body detection signal generation unit 2c, and the foreign body discrimination signal generation unit 3, when using the object 4 to be inspected including an object 71 to which a foreign body 72 having a surface reflectance lower than that of the surface of the object 71 adheres, as shown in FIG. 7.

Figure 13A:
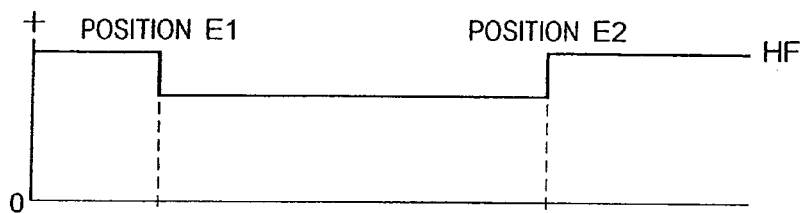
FIGS. 13A to 13E are charts showing signal waveforms of signals obtained in the detection of a foreign body in the foreign body detection apparatus having the third configuration.

The light spot 11 is irradiated on the object 4 to be inspected while scanning the object 4 in the direction of an arrow shown in FIG. 7, and a reflected light from the object 4 is received by the photodetector 8. Since the light intensity of the reflected light from the foreign body 72 is lower than that of the reflected light from the surface of the object 71, as shown in FIG. 13A, a photodetection signal HF having a waveform in which the signal level of the part of the foreign body 72 (between peripheral portions E1 and E2) is lower than the signal level of the surface of the object 71 is output from the photodetector 8.

Figure 13B:
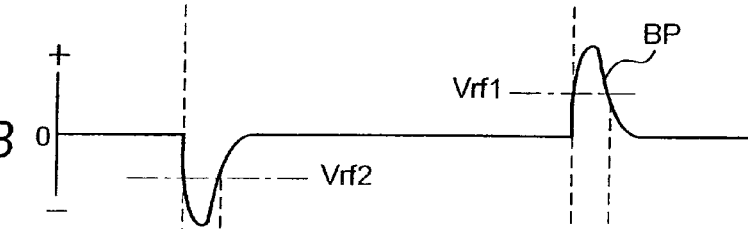

The photodetection signal HF output from the photodetector 8 is input to the band-pass filter 35 having the frequency band characteristic shown in FIG. 12 and a gain n. In the band-pass filter 35, low-frequency components and high-frequency components of the photodetection signal HF, i.e., unnecessary band components such as noise are removed, and as shown in FIG. 13B, a band-pass signal BP which passes a frequency band ft is output. The gain n may be equal to the gain of the subtractor 13 shown in FIG. 1 or 9.

Figure 13C:
Figure 13D:
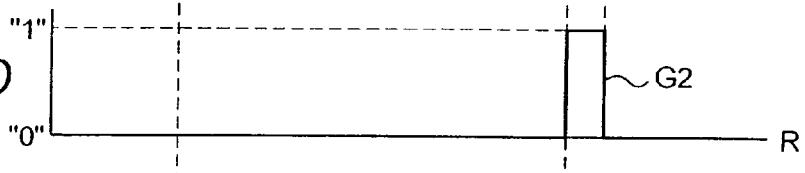
Figure 13E:
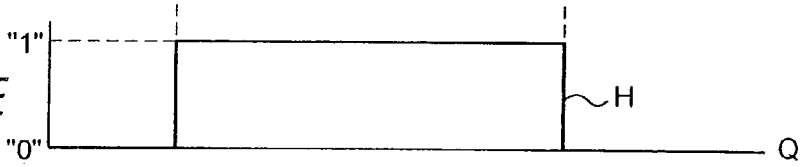

The band-pass signal BP output from the band-pass filter 35 is input to the comparators 14a and 14b to compare reference voltages Vrf1 and Vrf2 with the band-pass signal BP, respectively. At this time, a digital signal of "1" is output from comparators 14a and 14b when the absolute value of the voltage of the band-pass signal BP is larger than that of the respective reference voltages, and a digital signal of "0" is output from the comparators 14a and 14b when the absolute value of the voltage of the band-pass signal BP is smaller than that of the respective reference voltages. Therefore, the comparator 14a outputs a signal waveform G1 which is "1" at only the peripheral portion E1 and "0" at the other portions as shown in FIG. 13C. The comparator 14b outputs a signal waveform G2 which is "1" at only the peripheral portion E2, and "0" at the other portions as shown in FIG. 13D. The signals G1 and G2 are signals indicating a start peripheral portion and an end peripheral portion, respectively. Therefore, detection of the signal waveforms G1 and G2 makes it possible to determine that the foreign body is present between the portions where the signals G1 and G2 are detected. In addition, as shown in FIG. 13E, the signals G1 and G2 are input to an RS flipflop circuit 15 to generate a digital signal H which is "1" for a section between the peripheral portions E1 and E2. In this manner, a foreign body portion can be discriminated more easily.

The third configuration uses a band-pass filter to advantageously make a subtractor unnecessary. In addition, the third configuration can advantageously remove noise which is a high-frequency component.

Fourth Embodiment

Figure 14:
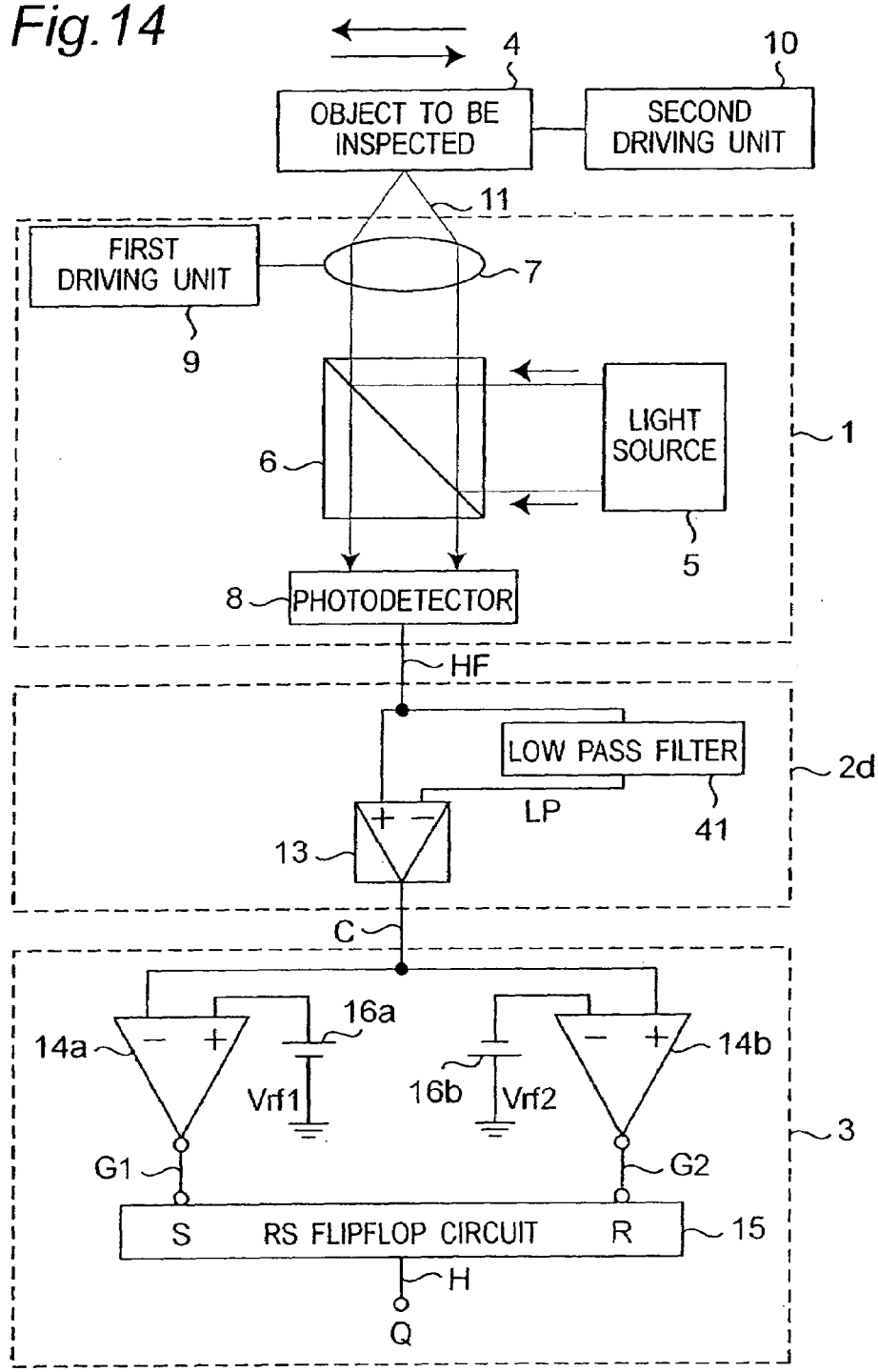
FIG. 14 is a block diagram showing the fourth configuration of the foreign body detection apparatus according to the present invention.

FIG. 14 is a block diagram showing the fourth configuration of the foreign body detection apparatus according to the present invention. The apparatus includes a photodetection signal generation unit 1, a foreign body detection signal generation unit 2d, and a foreign body discrimination signal generation unit 3. The configurations and operations of the photodetection signal generation unit 1 and the foreign body discrimination signal generation unit 3 are the same as those shown in FIG. 1.

The foreign body detection signal generation unit 2d includes a low-pass filter 41 for causing only the low-frequency components of a photodetection signal HF output from the photodetector 8 to pass through to generate a low-band signal LP, and a subtractor 13 for subtracting the low-band signal LP from the photodetection signal HF to generate a difference signal C.

A foreign body detection method achieved by the foreign body detection apparatus shown in FIG. 14 will be described below with reference to FIGS. 15A to 15F.

FIGS. 15A to 15F are charts showing signals output from the photodetection signal generation unit 1, the foreign body detection signal generation unit 2d, and the foreign body discrimination signal generation unit 3, respectively, when using an inspected object 4 to which a foreign body 72 with a surface reflectance lower than that of the object 71 adheres as shown in FIG. 7.

Figure 15:
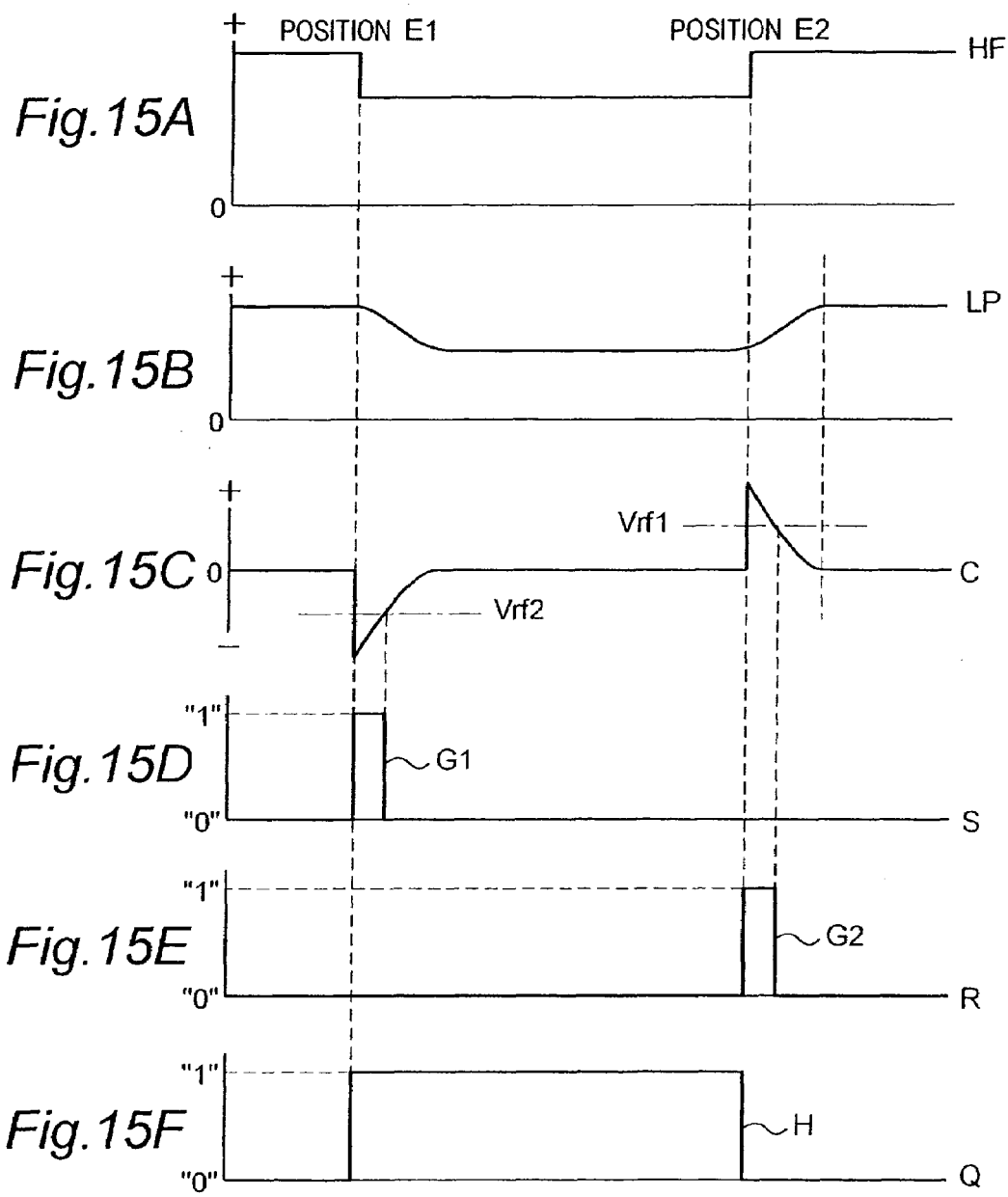
FIGS. 15A to 15F are charts showing waveforms of signals obtained in the detection of a foreign body in the foreign body detection apparatus having the fourth configuration.

The light spot 11 is irradiated on the inspected object 4 while scanning the inspected object 4 with the light spot in the direction of an arrow shown in FIG. 7, and a reflected beam from the inspected object 4 is received by the photodetector 8. Since the light intensity of the reflected beam from the foreign body 72 is lower than the light intensity of the reflected beam from the surface of the object 71, as shown in FIG. 15A, the photodetector 8 outputs the photodetection signal HF with a waveform in which the signal level of the part of the foreign body 72 (between a peripheral portion E1 and a peripheral portion E2) is lower than the that of the surface of the object 71.

The photodetection signal HF output from the photodetector 8 is input to a low-pass filter 41. The low-pass filter 41 outputs a low-band signal LP with a waveform obtained by causing only the low-frequency components of the photodetection signal HF to pass through, as shown in FIG. 15B. Since the high-frequency components of the photodetection signal HF are removed from the low-band signal LP, the signal is also free from noise.

The photodetection signal HF output from the photodetector 8 and the low-band signal LP output from the low-pass filter 41 are input to the subtractor 13 to subtract the low-band signal LP from the photodetection signal HF, that is, (HF−LP). The subtractor 13 outputs the difference signal C as shown in FIG. 15C. More specifically, a negative-pulse waveform is output due to HF<LP at the peripheral portion E1 of the foreign body 72, the waveform with 0 level is output because HF=LP at a position between the peripheral portions E1 and E2, and a positive-pulse waveform is output due to HF>LP at the peripheral portion E2 of the foreign body 72.

The difference signal C output from the subtractor 13 is input to comparators 14a and 14b to compare the reference voltages Vrf1 and Vrf2 with the difference signal C in voltage. A digital signal of "1" is output from the comparators 14a and 14b when the absolute value of the difference signal C is higher than the reference voltages Vef1 and Vrf2, and a digital signal of "0" is output when the absolute value of the difference signal C is lower than the absolute values of the reference voltages Vrf1 and Vrf2. Therefore, as shown in FIG. 15D, a signal G1 of "1" is output from the comparator 14a at only the peripheral portion E1, and a signal G1 of "0" is output at other portions. As shown in FIG. 15E, a signal G2 of "1" is output from the comparator 14b at only the peripheral portion E2, and a signal G2 of "0" is output at other portions. In this case, the signals G1 and G2 are signals indicating the leader and trailer of the periphery of the foreign body, respectively. Thus, detection of the signals G1 and G2 allows the presence of the foreign body between the portions where the signals G1 and G2 to be detected. In addition, the signals G1 and G2 are input to the RS flipflop circuit 15 to generate a signal H with a waveform which corresponds to a portion between the peripheral portions E1 and E2, as shown in FIG. 15F. In this manner, a foreign body portion can be more easily discriminated.

The fourth embodiment uses a low-pass filter to advantageously remove noise which is a high-frequency component. Since the low-pass filter is a filter having the simplest structure and can be constituted by a small number of parts, a reduction in cost and a reduction in size of the apparatus can be advantageously achieved.

Fifth Embodiment

Figure 16:
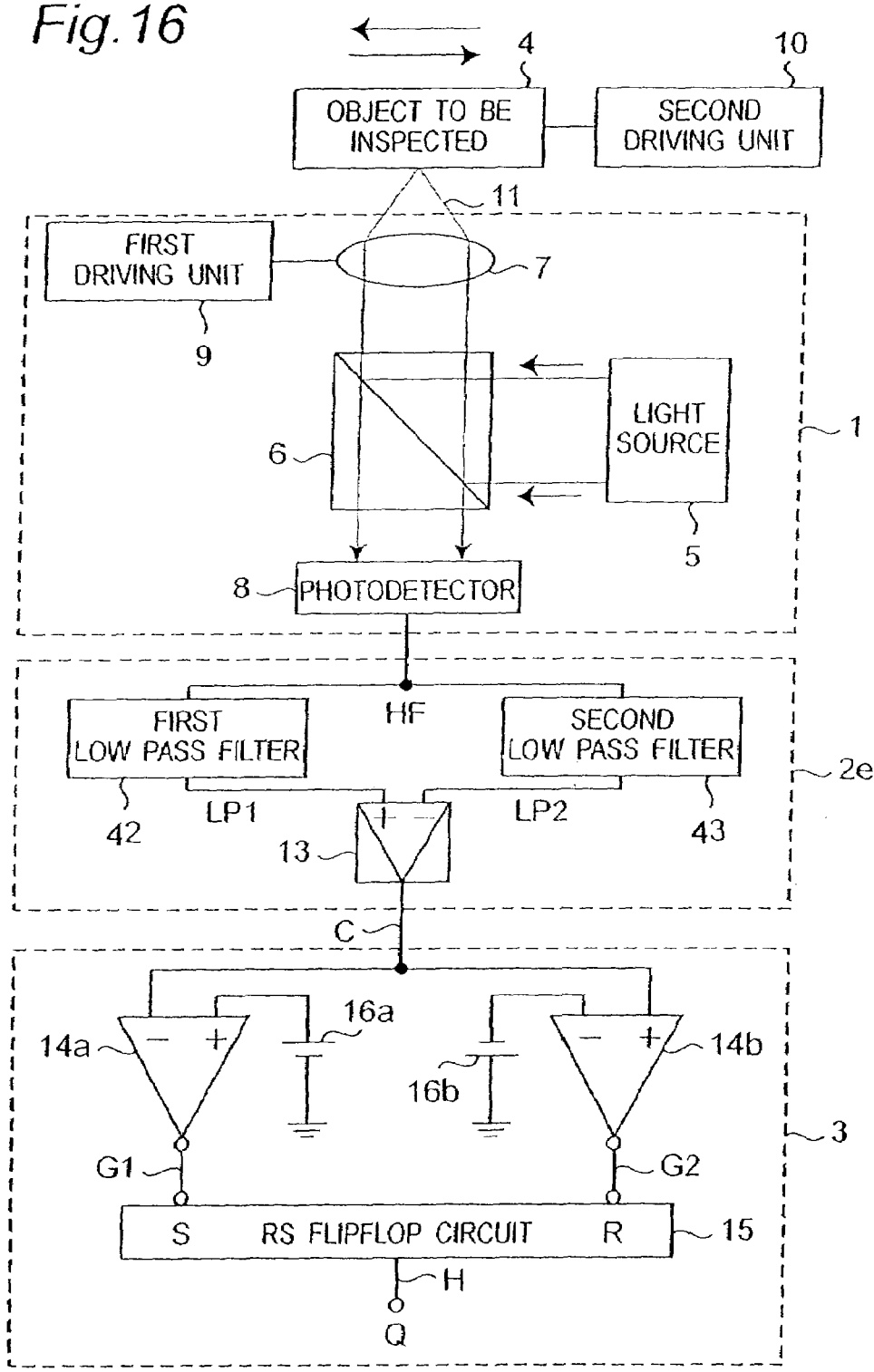
FIG. 16 is a block diagram showing the fifth configuration of the foreign body detection apparatus according to the present invention.

FIG. 16 is a block diagram showing the fifth configuration of the foreign body detection apparatus according to the present invention. The apparatus includes a photodetection signal generation unit 1, a foreign body detection signal generation unit 2e, and a foreign body discrimination signal generation unit 3. The configurations and operations of the photodetection signal generation unit 1 and the foreign body discrimination signal generation unit 3 are the same as those described in FIG. 1.

The foreign body detection signal generation unit 2e includes a first low-pass filter 42 (with cutoff frequency f3) for causing first low-frequency components included in a photodetection signal HF output from a photodetector 8 to pass through the filter 42 to generate a low-band signal LP1, a second low-pass filter 43 having a frequency characteristic different from that of the first low-pass filter 42 (with cutoff frequency f4), for causing second low-frequency components included in the photodetection signal HF to pass through the filter 43 to generate a low-band signal LP2, and a subtractor 13. The subtractor 13 subtracts the low-band signal LP2 output from the second low-pass filter 43 from the low-band signal LP1 output from the first low-pass filter 42 to generate a difference signal C. The cutoff frequencies f3 and f4 satisfy f3>f4.

A foreign body detection method achieved by the apparatus shown in FIG. 16 will be described below with reference to FIGS. 17A to 17G.

FIGS. 17A to 17G are charts showing signals output from the photodetection signal generation unit 1, the foreign body detection signal generation unit 2e, and the foreign body discrimination signal generation unit 3, respectively, when using the same object 4 to be inspected as described in FIG. 7.

Figure 17A:
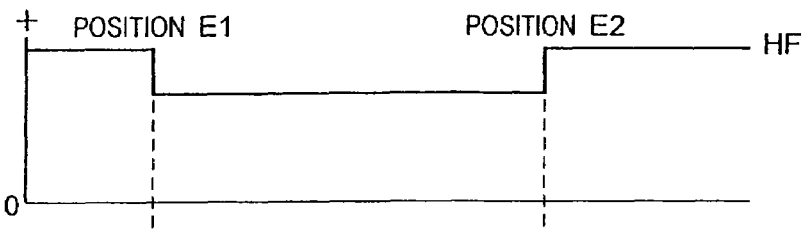
FIGS. 17A to 17G are charts showing signal waveforms of signals obtained in the detection of a foreign body in the foreign body detection apparatus having the fifth configuration.

According to the same method as described in the fourth embodiment, a reflected beam from the object 4 to be inspected is received by the photodetector 8. The photodetection signal HF shown in FIG. 17A is output from the photodetector 8.

Figure 17B:
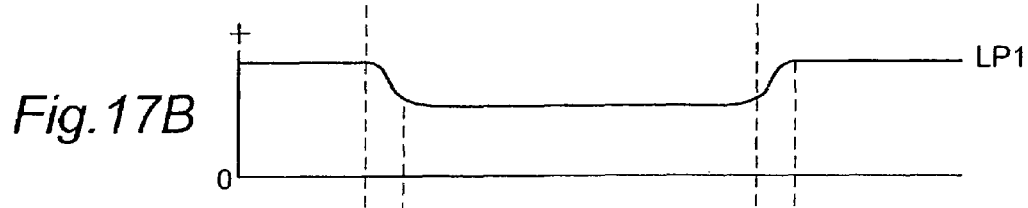
Figure 17C:
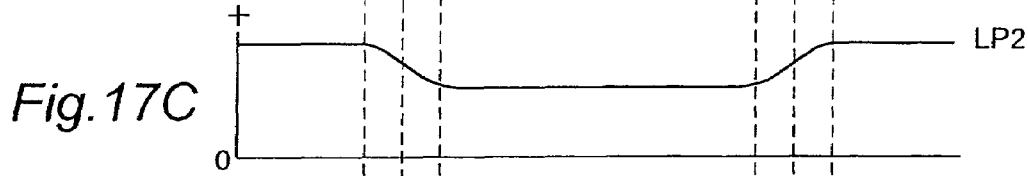
Figure 17D:
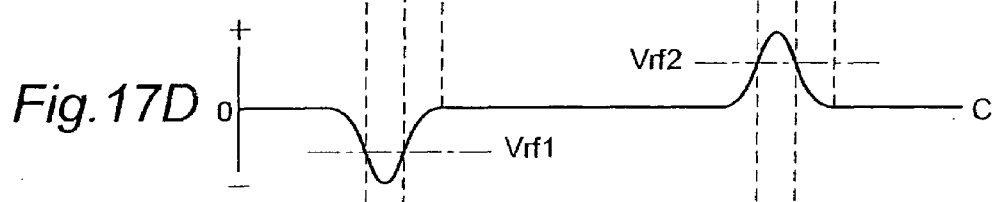

The photodetection signal HF output from the photodetector 8 is input to the first and second low-pass filters 42 and 43. The first low-pass filter 42 outputs the low-band signal LP1 obtained by causing only the first low-frequency components of the photodetection signal HF to pass through the filter 42, as shown in FIG. 17B. The second low-pass filter 43 outputs the low-band signal LP2 obtained by causing only the second low-frequency components of the photodetection signal HF to pass through the filter 43, as shown in FIG. 17C.

The low-band signal LP1 and the low-band signal LP2 are input to the subtractor 13 for subtraction. The difference signal C is output from the subtractor 13. More specifically, at the peripheral portion E1 of the foreign body 72, LP1>LP2 is satisfied and a negative-pulse waveform is output. At the region between the peripheral portions E1 and E2, LP1=LP2 is satisfied and a waveform of 0 level is output. At the peripheral portion E2 of the foreign body 72, LP1<LP2 is satisfied and a positive-pulse waveform is output.

Figure 17E:
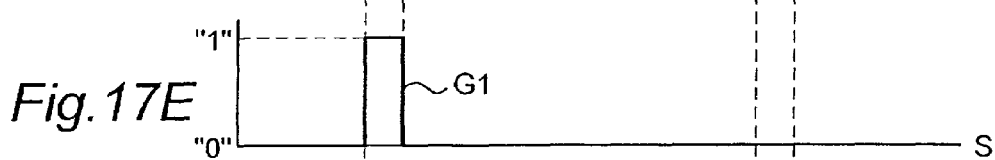
Figure 17F:
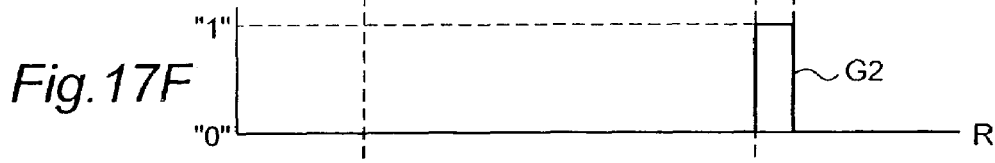
Figure 17G:
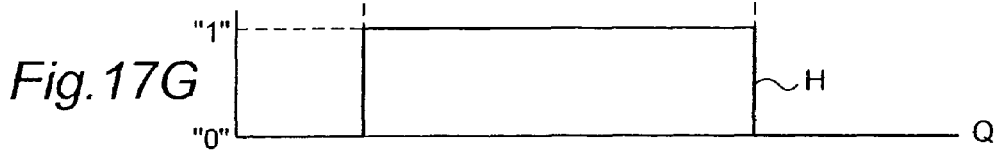

The difference signal C output from the subtractor 13 is input to comparators 14a and 14b. As shown in FIG. 17E, the comparator 14a outputs a signal G1 which has a value of "1" at only the peripheral portion E1, and "0" at other portions. As shown in FIG. 17F, the comparator 14b outputs a signal G2 which has a value of "1" at only the peripheral portion E2, and "0" at other portions. Furthermore, the signals G1 and G2 are input to an RS flipflop circuit 15 to generate a signal I with a waveform with a value of "1" in which a portion between the peripheral portions E1 and E2 is converted, as shown in FIG. 17G. In this manner, the region of a foreign body can be more easily discriminated.

Sixth Embodiment

Figure 18:
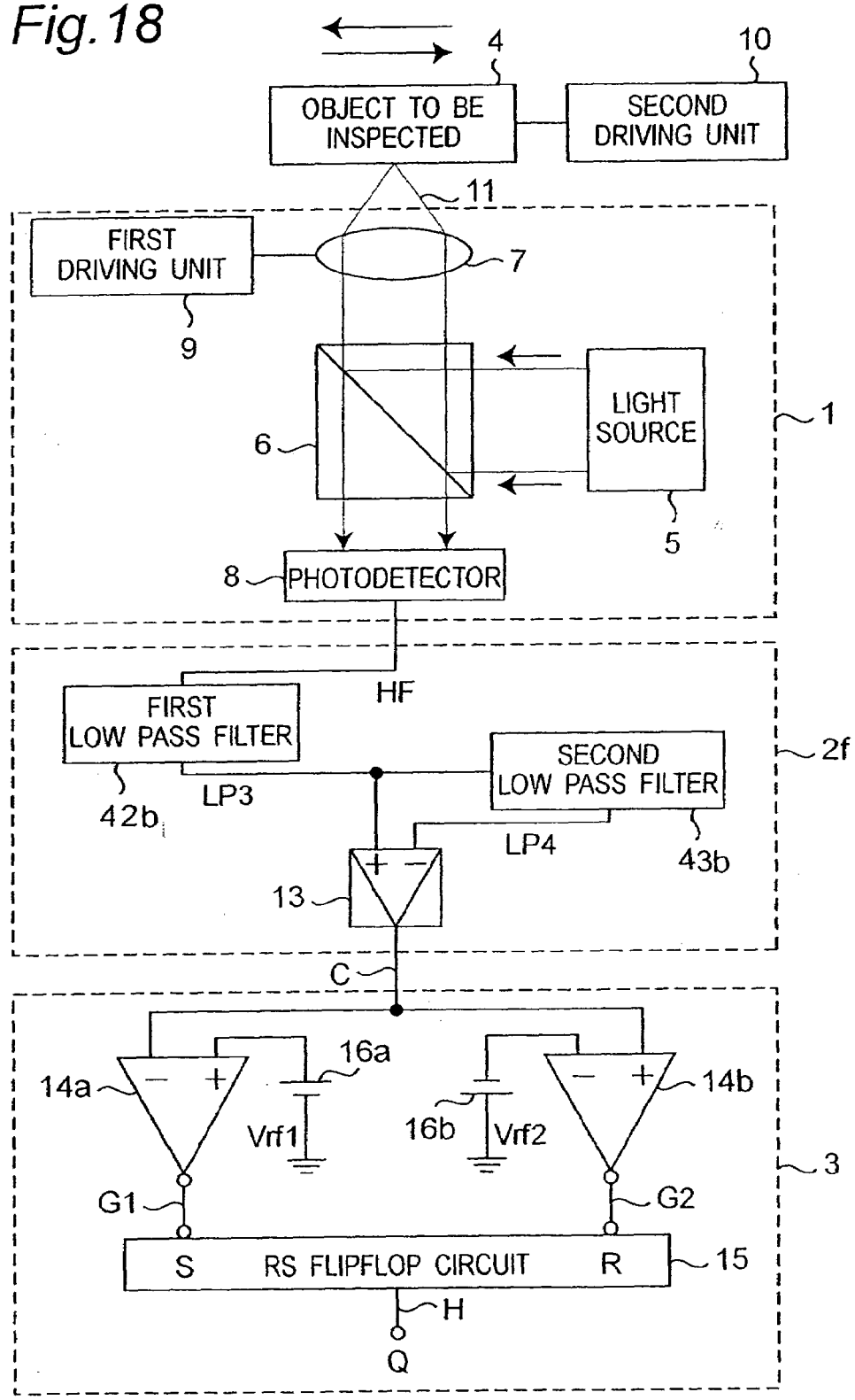
FIG. 18 is a block diagram showing the sixth configuration of the foreign body detection apparatus according to the present invention.

FIG. 18 is a block diagram showing the sixth configuration of the foreign body detection apparatus according to the present invention. The apparatus includes a photodetection signal generation unit 1, a foreign body detection signal generation unit 2f, and a foreign body discrimination signal generation unit 3. The configurations of the photodetection signal generation unit 1 and the foreign body discrimination signal generation unit 3 are the same as those described in FIG. 1.

The foreign body detection signal generation unit 2f includes a first low-pass filter 42b for causing first low-frequency components of a photodetection signal HF output from a photodetector 8 to pass through to generate a low-band signal LP3, a second low-pass filter 43b for causing second low-frequency components of the low-band signal LP3 from the first low-pass filter 42b to pass through to generate a low-band signal LP4, and a subtractor 13. The frequency characteristics of the first low-pass filter 42b and the second low-pass filter 43b are different. The subtractor 13 subtracts the low-band signal LP4 output from the second low-pass filter 43b from the low-band signal LP3 output from the first low-pass filter 42b to generate a difference signal C.

A foreign body detection method achieved by the foreign body detection apparatus shown in FIG. 18 will be described below with reference to FIGS. 19A to 19G.

FIGS. 19A to 19G are charts showing, when using the same object 4 to be inspected as described in FIG. 7, signals output from the photodetection signal generation unit 1, the foreign body detection signal generation unit 2f, and the foreign body discrimination signal generation unit 3.

Figure 19:
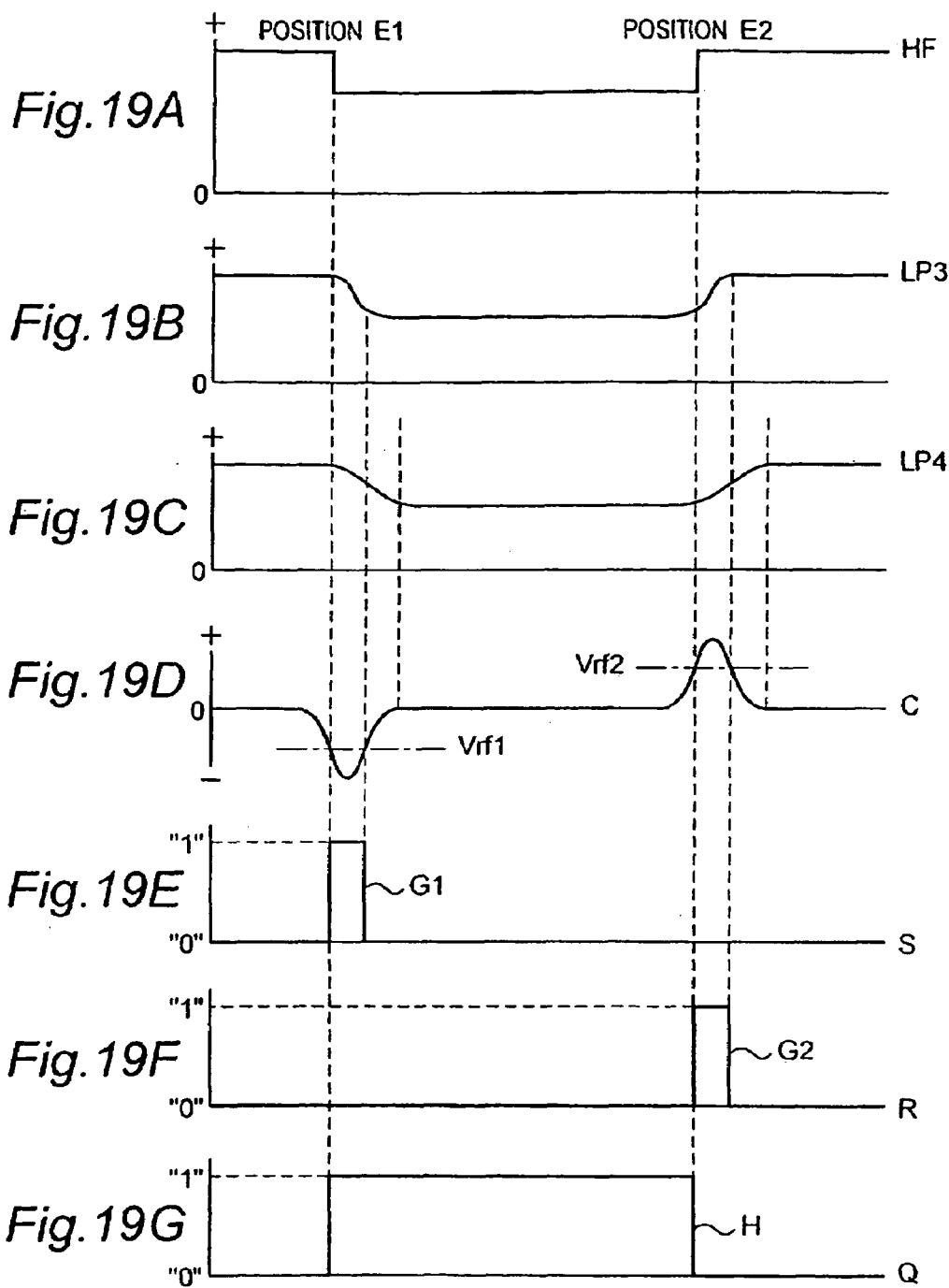
FIGS. 19A to 19G are charts showing signal waveforms of signals obtained in the detection of a foreign body in the foreign body detection apparatus having the sixth configuration.

By the same method as described in the first embodiment, a reflected beam from the object 4 to be inspected is received by the photodetector 8. A photodetection signal HF shown in FIG. 19A is output from the photodetector 8.

The photodetection signal HF output from the photodetector 8 is input to the first low-pass filter 42b. From the first low-pass filter 42b, as shown in FIG. 19b, the low-band signal LP3 obtained by causing only the first low-frequency components of the photodetection signal HF to pass through the first low-pass filter 42b is output.

The low-band signal LP3 output from the first low-pass filter 42b is input to the second low-pass filter 43b. From the second low-pass filter 43b, as shown in FIG. 19C, the low-band signal LP4 obtained by causing only the second low-frequency components of the photodetection signal HF to pass through the second low-pass filter 43b is output.

The low-band signal LP3 and the low-band signal LP4 are input to the subtractor 13 and subtracted. A difference signal C shown in FIG. 19D is output from the subtractor 13. More specifically, LP3<LP4 is satisfied at the peripheral portion E1 of the foreign body 72, and a negative-pulse waveform is output. LP3=LP4 is satisfied between the peripheral portion E1 and the peripheral portion E2, and a waveform of 0 level is output. LP3>LP4 is satisfied at the peripheral portion E2 of the foreign body 72, and a positive-pulse waveform is output.

The difference signal C output from the subtractor 13 is input to comparators 14a and 14b. As shown in FIG. 19E, a signal G1 of "1" is output from the comparator 14a at only the peripheral portion E1, and a signal G1 of "0" is output from the comparator 14a at other portions. As shown in FIG. 19F, a signal G2 of "1" is output from the comparator 14b at only the peripheral portion E2, and a signal G2 of "0" is output from the comparator 14b at other portions. Therefore, the detection of the signals G1 and G2 makes it possible to judge that the foreign body is present between the portions where the signals G1 and G2 are detected. In addition, the signals G1 and G2 are input to an RS flipflop circuit 15, thus generating a signal H having a waveform in which a portion between the peripheral portions E1 and E2 is converted to "1", as shown in FIG. 19G. With this configuration, the first low-pass filter 42b and the second low-pass filter 43b can remove high-frequency components of the photodetection signal HF, so that a foreign body portion can be easily discriminated. The first low-pass filter 42b and the second low-pass filter 43b shown in FIG. 18 may have equal frequency characteristics or difference frequency characteristics. When the first low-pass filter 42b and the second low-pass filter 43b have the equal frequency characteristics and are regarded in the digital signal processing, the low-band signal LP3 of the first low-pass filter 42b is stored in a memory. The signal stored in the memory may be applied to the first low-pass filter 42b again so that the signal LP4 which is equivalent to the output signal from the second low-pass filter 43b can be obtained. In this manner, a configuration using only one filter may be advantageously achieved.

Seventh Embodiment

Figure 20:
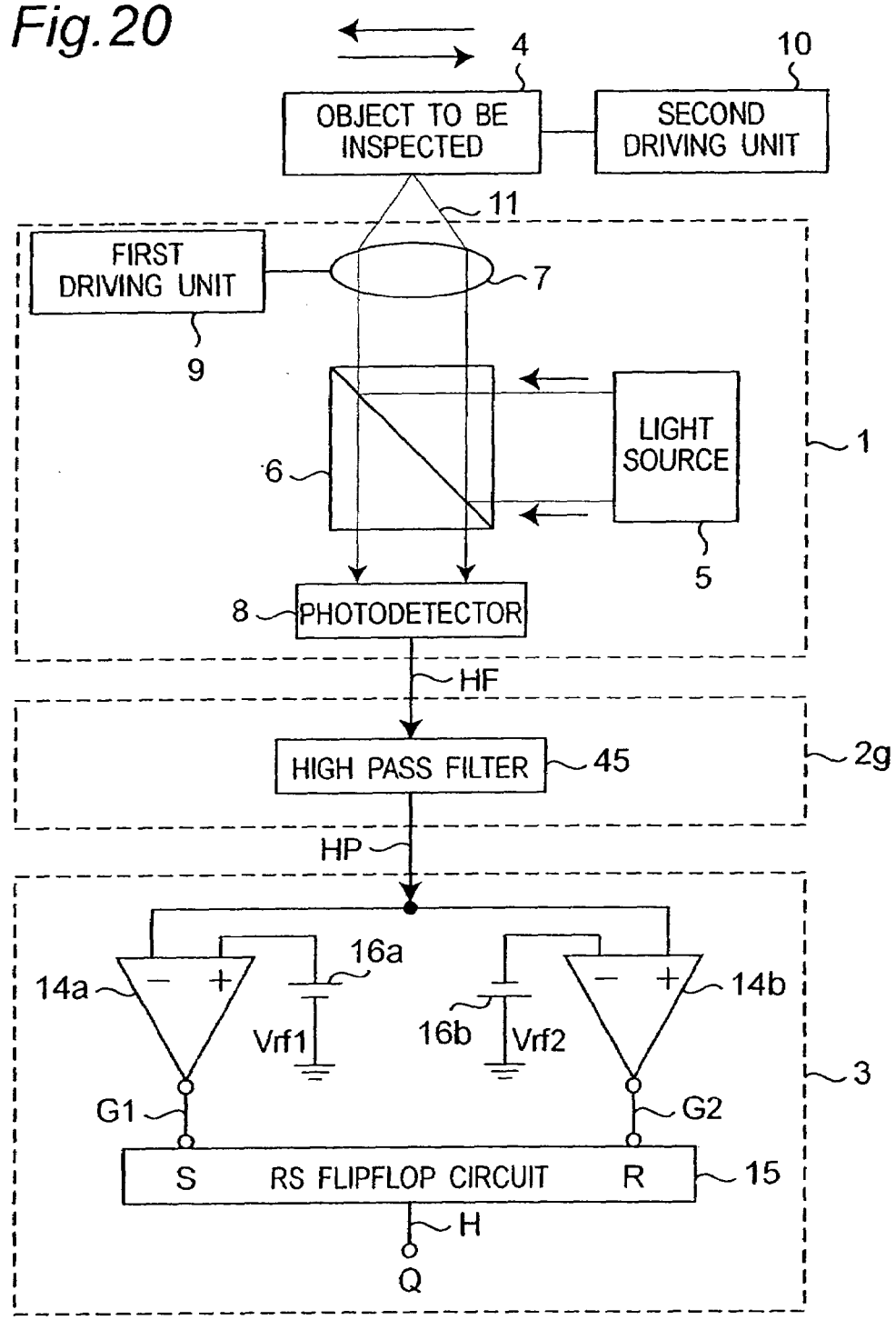
FIG. 20 is a block diagram showing the seventh configuration of a foreign body detection apparatus according to the present invention.

FIG. 20 is a block diagram showing the seventh configuration of the foreign body detection apparatus according to the present invention. The apparatus includes a photodetection signal generation unit 1, a foreign body detection signal generation unit 2g, and a foreign body discrimination signal generation unit 3. The configurations and operations of the photodetection signal generation unit 1 and the foreign body discrimination signal generation unit 3 are the same as those shown in FIG. 1.

Figure 21:
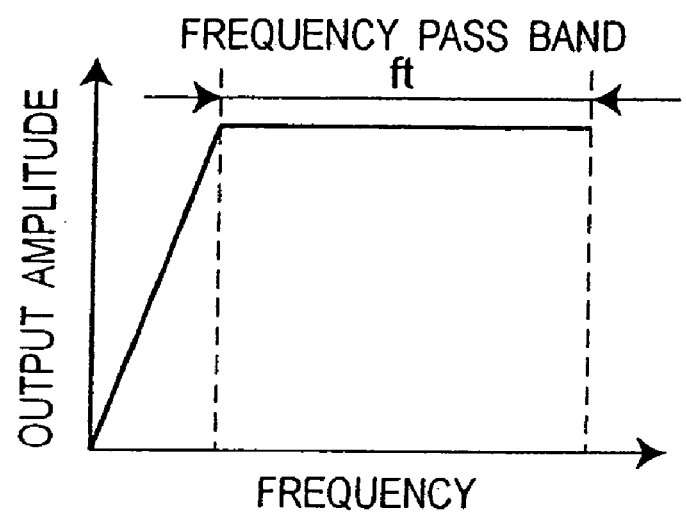
FIG. 21 is a graph showing a passing band characteristic of a high-pass filter of the foreign body detection apparatus having the seventh configuration.

The foreign body detection signal generation unit 2g includes a high-pass filter 45 for removing low-frequency components from a signal HF output from a photodetector 8 to generate a high-frequency band-pass signal HP (to be referred to as a HP signal hereinafter). FIG. 21 shows the frequency characteristic of the high-pass filter 45.

A foreign body detection method achieved by the foreign body detection apparatus shown in FIG. 20 will be described below with reference to FIGS. 22A to 22E.

FIGS. 22A to 22E are charts showing signals output from the photodetection signal generation unit 1, the foreign body detection signal generation unit 2g, and the foreign body discrimination signal generation unit 3, when using, as the object 4 to be inspected, an object 71 as shown in FIG. 7 to which a foreign body 72 having a surface reflectance lower than that of the surface of the object 71 adheres.

The light spot 11 is irradiated on the object 4 (71) to be inspected while scanning the object 4 (71) to be inspected in the direction of an arrow shown in FIG. 7, and a reflected beam from the object 4 (71) to be inspected is received by the photodetector 8. Since the light intensity of the reflected beam from the foreign body 72 is lower than the light intensity of the reflected beam from the surface of the object 71, the level of signal from the foreign body 72 portion (between the peripheral portion E1 and the peripheral portion E2) is lower than the level of a signal from the object 71, as shown in FIG. 22A. Thus, a signal HF is output from the photodetector 8.

The signal HF output from the photodetector 8 is input to a high-pass filter 45 having the frequency band characteristic shown in FIG. 21. Low-frequency components of the photodetection signal HF are removed, and a signal HP passing through a frequency band ft is output from the high-pass filter 45, as shown in FIG. 22B.

The signal HP output from the high-pass filter 45 is input to the comparators 14a and 14b, and is compared with reference voltages Vrf1 and Vrf2. As shown in FIG. 22C, the comparator 14a outputs a digital signal G1 which is "1" at only the peripheral portion E1, and "0" at the other portions. As shown in FIG. 22D, the comparator 14b outputs a digital signal G2 which is "1" at only the peripheral portion E2, and "0" at the other portions. Therefore, the detection of the signals G1 and G2 makes it possible to determine that the foreign body is present between the portions where the signals G1 and G2. In addition, the signals G1 and G2 are input to an RS flipflop circuit 15 to generate a signal H having a waveform in which a portion between the peripheral portions E1 and E2 is converted into "1", as shown in FIG. 22E. Thus, the foreign body portion can be more easily discriminated. With this configuration, the subtractors 13 shown in FIGS. 1, 2, 4, and 6 which are block diagrams of 1, 2, 4, 5 and 6-th configurations can be advantageously omitted. When the high-pass filter is constituted by an analog circuit, the high-pass filter can be constituted by only one capacitor and one resistor. Thus, the number of parts can be reduced, and reductions in cost and in size can be advantageously achieved.

Eighth Embodiment

Figure 23:
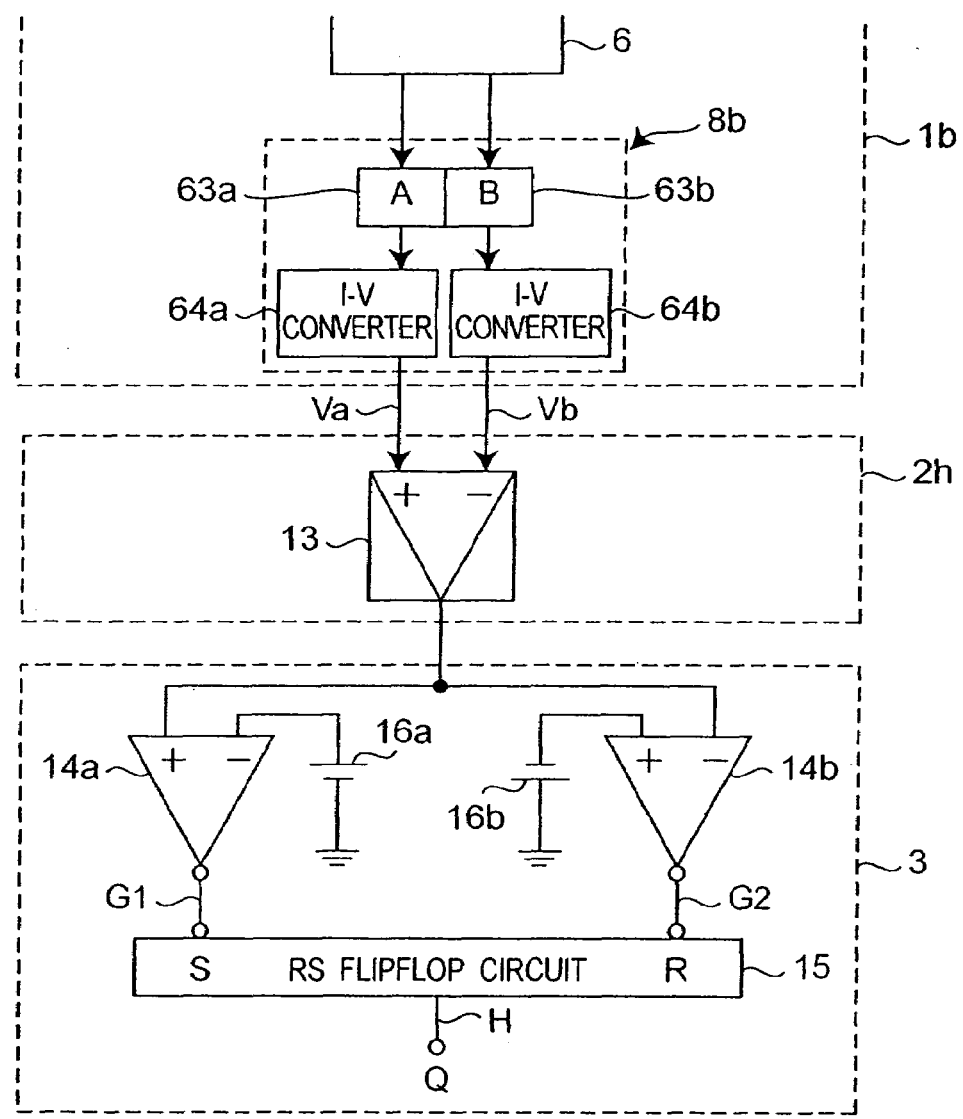
FIG. 23 is a block diagram showing the eighth configuration of the foreign body detection apparatus according to the present invention.

FIG. 23 is a block diagram showing the eighth configuration of the foreign body detection apparatus according to the present invention. The foreign body detection apparatus includes a photodetection signal generation unit 1b, a foreign body detection signal generation unit 2h, and a foreign body discrimination signal generation unit 3.

The photodetection signal generation unit 1b basically has the same configuration as that of the photodetection signal generation unit 1 according to the first embodiment, except for the configuration of the photodetector 108b. More specifically, the photodetector 108b of this embodiment uses a photoelectric conversion element having two divided regions 63a and 63b. In particular, when an object to be inspected is an optical disk, the optical disk 100 is arranged such that its surface is located at a focal point of an object lens, and the standard deviation of the wave aberration of a laser beam on the surface of the optical disk is preferably set to be 0.07 or more times the wavelength of the laser beam.

The foreign body detection signal generation unit 2h includes a subtractor 13 which calculates a difference between a voltage Va output from a I-V converter 64a connected to a photoelectric element 63a and a voltage Vb output from an I-V converter 64b connected to a photoelectric element 63b to generate a difference signal (Va−Vb).

The foreign body discrimination signal generation unit 3 is the same as that described in the first embodiment.

FIGS. 24A to 24D are charts showing a difference signal waveform and an output signal waveform from comparators 14a and 14b, when an object to be inspected is an optical disk, and when a foreign body 72 having a surface reflectance lower than that of the optical disk 100 adheres to the surface of the optical disk 100.

When a portion from an outside edge portion E1 to an outside edge portion E2 of the foreign body 72 is scanned by a light spot 11 in the direction of an arrow, a difference voltage waveform as shown in FIG. 24A is output from the subtractor 13. A light intensity of a reflected beam sharply changes and Va>Vb is satisfied at the outside edge portion E1, and thus a pulse waveform is output. Va=Vb is satisfied between the portions E1 and E2, and thus a waveform of 0 level is output. A light intensity of a reflected beam sharply changes and Va<Vb is satisfied at the outside edge portion E2 similarly to the portion E1, and thus a pulse waveform is output.

When the difference voltage is input to the comparators 14a and 14b, the comparator 14a outputs a digital signal waveform G1 which is "1" at only the peripheral portion E1, and "0" at the other portions, as shown in FIG. 24B. The comparator 14b outputs, as shown in FIG. 24C, a digital signal G2 which is "1" at only the peripheral portion E2, and "0" at the other portions. Therefore, based on the signals G1 and G2, the peripheral boundary of the foreign body can be detected. In addition, the signals G1 and G2 are input to a flipflop circuit 15 to generate a signal H having a waveform in which a portion between the peripheral portions E1 and E2 is converted into "1", as shown in FIG. 24D. In this configuration, when the standard deviation of the wave aberration of a laser beam is 0.07 or less times the wavelength of the laser beam, the level of the difference signal (Va−Vb) shown in FIG. 24A may decrease, and detection cannot be preferably performed. Therefore, the standard deviation is preferably set to be 0.07 or more times the wavelength of the laser beam. For the light spot 11 and the photodetector 108b, the photoelectric elements 63a and 63b are divisionally aligned with reference to the longitudinal direction of the track of the optical disk as shown in FIG. 24E. They are arranged such that an image formed by a reflected beam from the surface of the optical disk 100 is received by the photoelectric elements 63b and 63a in this order.

The foreign body detection apparatus according to the present invention described in the above embodiment can be applied to the following devices typically:

a foreign body inspection apparatus used in processes of manufacturing an electronic image device or a semiconductor integrated circuit;

an optical disk apparatus for recording and reproducing information on/from a recording medium such as a CD (Compact Disk), an LD (Laser Disk), a DVD (Digital Versatile Disk), a phase-change optical recording medium, a pigmentary change recording medium, or a magneto-optical recording medium;

a system with an optical disk apparatus, such as a computer, a computer system, a computer network system, or an MFP (Multi-Function product); and an optical disk apparatus to be equipped on an automobile, a train, an airplane, or a ship.

In particular, when the foreign body detection apparatus is applied to the optical disk apparatus and the system with the optical disk apparatus, the following advantages can be achieved.

1) An optical disk having a high information recording density can be used.

2) Problems such as erroneous recording/reproducing and mistracking caused by a foreign body adhering to the optical disk surface can be avoided.

3) Recording/reproducing reliability can be improved by detecting a foreign body to give an alarm and to remove the foreign body by a cleaning means.

An optical disk apparatus having the foreign body detection apparatus according to the present invention and applications of the optical disk apparatus will be described below.

Ninth Embodiment

Figure 25:
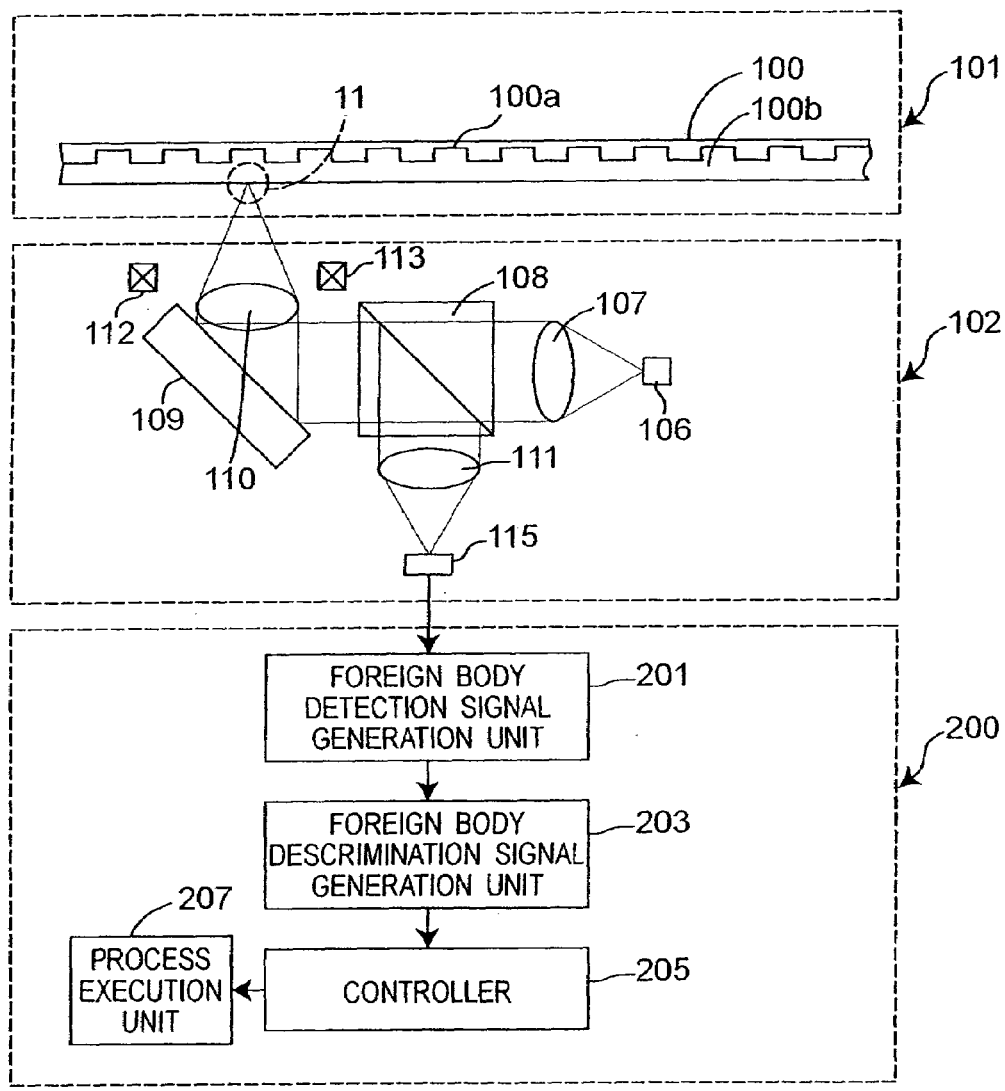
FIG. 25 is a block diagram showing a configuration of an optical disk apparatus according to the present invention.

FIG. 25 is a block diagram showing a configuration of an optical disk apparatus according to the present invention.

The optical disk apparatus is a device for recording or reproducing data to/from an optical disk 100 having an information recording layer 100a and a transparent layer (light-transmitting layer) 100b. The optical disk apparatus includes an optical disk drive unit 101, an optical head unit 102, and a foreign body detection process unit 200.

The optical disk drive unit 101 is a mechanical unit for rotatably driving the optical disk 100 and includes a turntable, a spindle motor (not shown), and the like. In the information recording layer 100a, a recording material film is formed on guide grooves for tracking and a land portion located between the guide grooves by a sputtering method, a vacuum evaporation method, a spin coating method, or the like.

The optical head unit 102 includes a laser beam source 106 for emitting a laser beam, an optical system, a focus actuator 112, a tracking actuator 113, and a photodetector 115. As a light source which is suitable for detecting a foreign body on an optical disk, in addition to the laser beam source 106, an electric light bulb, a halogen lamp, or the like can be used. For a laser beam source, a semiconductor laser is preferably used for a reduction in size and power.

The optical system includes a collimate lens 107, a beam splitter 108, a reflecting mirror 109, an object lens 110, and a detection lens 111.

The focus actuator 112 moves the object lens 110 in a direction perpendicular to the surface of the optical disk 100 to change the focal point of the object lens 110.

The tracking actuator 113 moves the object lens 110 in a direction perpendicular to the longitudinal direction of the track of the optical disk 100 to change an irradiation position of a laser beam 105.

The photodetector 115 has the same configuration as that of the photodetector 8 or 8b in the above embodiments.

The operation of the optical head unit 102 will be described below. The focus actuator 112 moves the object lens 110 to irradiate a light spot 11 which is obtained by converging the laser beam in a desired size, on the surface of the optical disk 100. The laser beam reflected on the surface of the optical disk 100 is received by the photodetector 115 through the object lens 110, the reflecting mirror 109, the beam splitter 108, and the detection lens 111, and a signal HF is output from the photodetector 115.

The diameter and shape of the light spot 11 and a scanning method for the light spot 11 irradiated on the optical disk 100 are the same as those in the first embodiment. It is noted that a foreign body such as bubble or a foreign material being present inside the transparent layer (light-transmitting layer) 100b of the optical disk 100 can be detected by forming the light spot 11 in the transparent layer 100b.

The foreign body detection process unit 200 includes a foreign body detection signal generation unit 201 for detecting a foreign body based on the photodetection signal HF output from the photodetector 115, a foreign body discrimination signal generation unit 203 for discriminating a position and a region to which a foreign body adheres based on the foreign body detection signal output from the foreign body detection signal generation unit 201, a control unit (controller) 205 for controlling a predetermined process to be executed when the presence of a foreign body is detected based on an output signal (to be referred to as a "foreign body discrimination signal" hereinafter) from the foreign body discrimination signal generation unit 203, and a process execution unit 207 for executing the predetermined process to be executed upon the detection of a foreign body based on a control signal from the control unit 205.

The foreign body detection signal generation unit 201 and the foreign body discrimination signal generation unit 203 have the same configurations as those of the foreign body detection signal generation units 2a to 2h and the foreign body discrimination signal generation unit 3 in the foreign body detection apparatuses described in the first to eighth embodiments, and perform the same operations.

The control unit 205 outputs control information for operating the process execution unit 207 based on the foreign body discrimination signal from the foreign body discrimination signal generation unit 203.

The process execution unit 207 includes a notification means for notifying an operator of the presence of a foreign body upon the detection of a foreign body. As the notification means, a loudspeaker for generating an alarm sound or voice, a sound output means such as a buzzer, a warning light, a display means for displaying a warning image, or other means for notifying an operator of the presence of a foreign body through information (stimulus) such as vibration or temperature which can be sensed by a person may be used.

The process execution unit 207 includes a device for automatically stopping a recording/reproducing operation of an optical disk when a foreign body is detected, or a device which automatically switches a recording/reproducing operation of/from the optical disk from the optical disk apparatus in execution of recording/reproduction to another optical disk apparatus. In addition, the process execution unit 207 includes a device for controlling a recording/reproducing operation to record or reproduce data while removing only a portion to which a foreign body adheres upon the detection of a foreign body, a device for automatically ejecting an optical disk from the disk drive mechanism unit, and a means for performing a process to a foreign body such as a cleaning mechanism for cleaning the entire surface of an optical disk or only a portion of the optical disk to which a foreign body adheres. Depending on the targets of the optical disk apparatus and the system, one or a plurality of means are appropriately selected from the above means and built in the process execution unit 207.

The foreign body discrimination signal generation unit 203 according to the present invention is considerably advantageous as a means for specifying a position and a region to which a foreign body adheres for partial recording, reproducing, and cleaning operations of an optical disk. However, depending on the targets of the optical disk apparatus and the system, the partial recording, reproducing, and cleaning operations may not be required. In such a case, the foreign body discrimination signal generation unit 203 is not always required, and a foreign body detection signal output from the foreign body detection signal generation unit 201 may be directly input to the control unit 205.

The optical disk apparatus can be applied to an optical disk apparatus built-in system such as a computer, a computer system, a computer network system, or an MFP (Multi-Function product), and an optical disk apparatus mounted on an automobile, a train, an airplane, or a ship.

Tenth Embodiment

Figure 26:
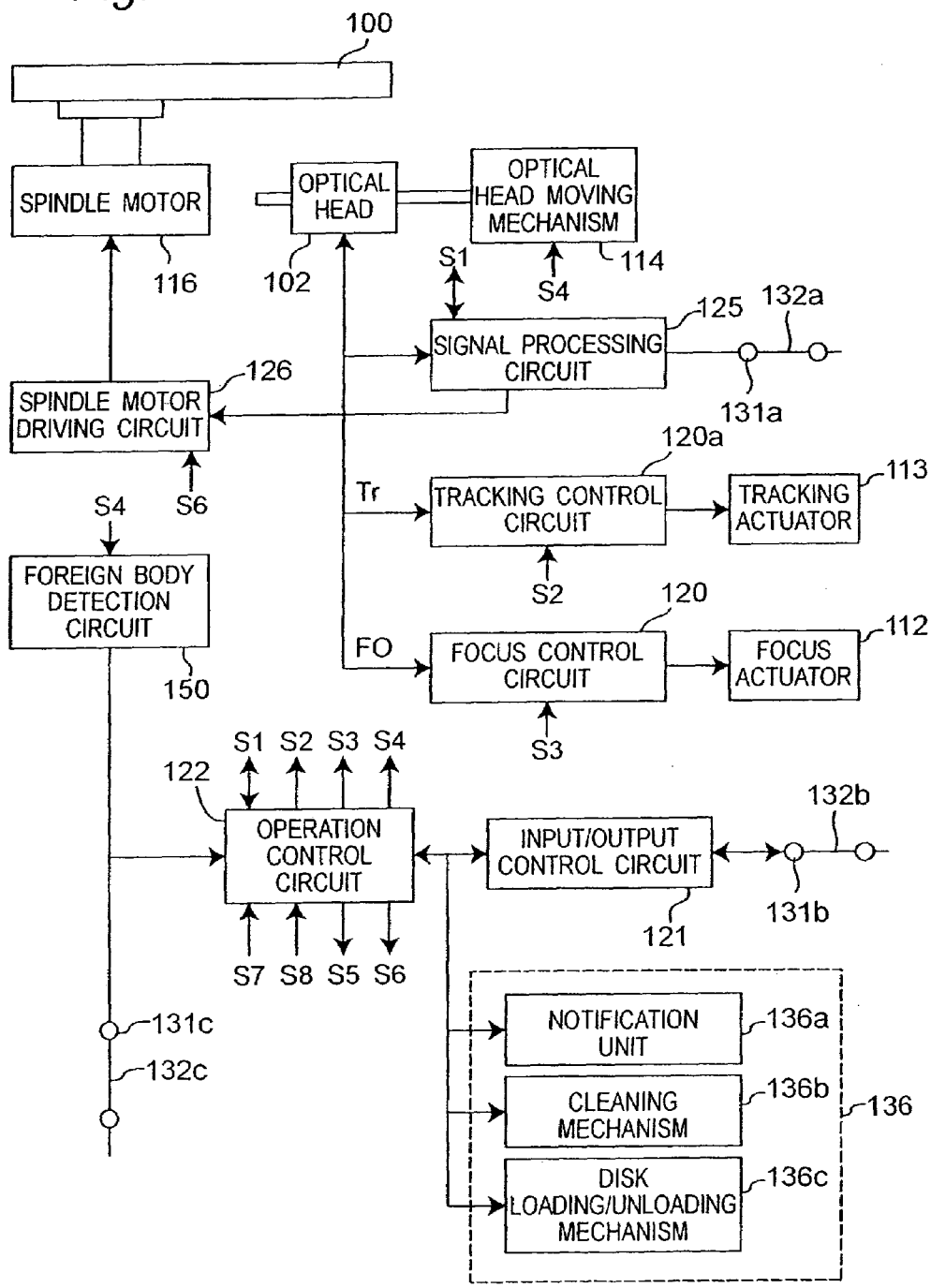
FIG. 26 is a block diagram showing a more detailed configuration of the optical disk apparatus according to the present invention.

FIG. 26 is a block diagram showing a more detailed configuration of the optical disk apparatus according to the present invention. As shown in FIG. 26, the optical disk apparatus includes constituent elements such as an optical head 102, a focus drive control circuit 120, an input/output control circuit 121, a operation control circuit 122, a signal processing circuit 125, a foreign body detection circuit 150, and a process execution unit 136. In the optical disk apparatus, the signal processing circuit 125, the input/output control circuit 121, and the foreign body detection circuit 150 are connected to external transmission paths 132a to 132c through terminals 131a to 131c, respectively.

Figure 27A:
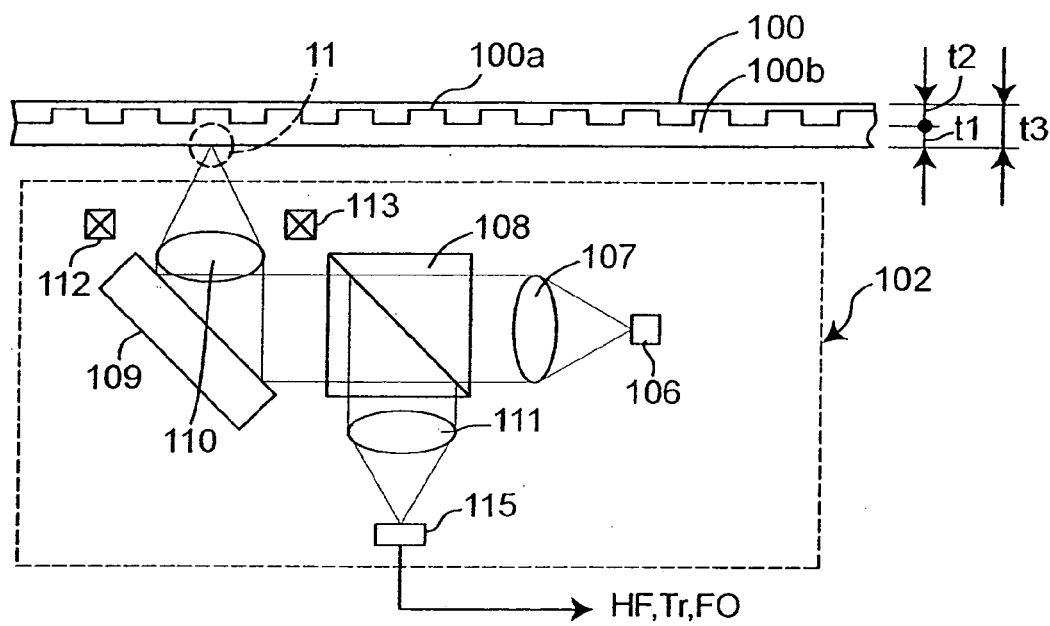
FIG. 27A is a block diagram showing the configuration of an optical head unit in the optical disk apparatus according to the present invention.

FIG. 27A is a diagram showing a detailed configuration of the optical head unit 102 included in the optical disk apparatus. The optical head unit 102 generates a light beam for recording/reproducing data and detecting a foreign body. As the laser beam source 106, a semiconductor laser having a wavelength of about 200 nm to 800 nm used for a recording/reproducing operation is used. The refraction index and numerical aperture of the object lens 110 are appropriately selected depending on the type and configuration of the optical disk 100. For example, when the optical disk 100 is a phase-change recording medium having the following specifications, an object lens having a refraction index n of 1.3 to 3.0 and a numerical aperture NA of 0.45 to 0.95 is used.

<Configuration of Phase-change Recording Medium>

Figure 27B:
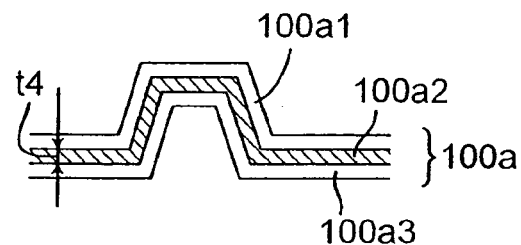
FIG. 27B is a diagram showing the structure of an information recording layer.

FIG. 27B is an enlarged diagram of the information recording layer 100a. The information recording layer 100a has dielectric layers 100a1 and 100a3. As material used in the dielectric layers 100a1 and 100a3, ZnS, ZnS—SiO2, SiO2, SiNx, or the like is used. The information recording layer 100a further has a recording layer 100a2 using a phase-change material between the dielectric layers 100a1 and 100a3. As the material of the recording layer 100a2, e.g., Ge—T—Sb or In—Ag—Te—Sb, or the like is used. The thickness of the recording layer 100a2 is represented by t4.

The thicknesses of the transparent layer and the recording layer fall within the following ranges:

the thickness of the transparent layer 100b (t1): 0.01 μm to 1200 μm, the thickness of the recording layer 100a2 (t4): $\lambda/(40 \times n)$ to $\lambda/(4 \times n')$ (where $\lambda$ is the wavelength of the semiconductor laser, and n' is the refraction index of the recording layer 100a2)

the thickness of the optical disk (t3): 0.05 mm to 2.4 mm.

The object lens 110 is designed such that an aberration is minimum when the optical spot is in focus on the information recording layer 100a of the optical disk 100.

Returning to FIG. 26, the focus drive control circuit 120 controls the object lens 110 based on a focus signal F0 from the optical head 102 such that the object lens 110 is in focus on the information recording layer 100a. A tracking control circuit 120a performs tracking control based on a tracking signal Tr from the optical head 102 such that the light spot follows the information track (not shown) of the optical disk 100. A optical head moving mechanism 114 moves the optical head 102 in the radial direction of the optical disk 100.

In a reproducing operation, a reproduction signal read from the optical disk 100 through the optical head 102 is converted into video/audio signals or the like by the signal processing circuit 125, is subjected to a process such as D/A conversion, and is output to the outside through the external transmission path 132a. In the recording operation, video/audio information inputted through the external transmission path 132a is subjected to a process such as D/A conversion in the signal processing circuit 125 and then recorded on the optical disk 100 through the optical head 102. These recording or reproducing operations are controlled by the operation control circuit 122. These operations are the same as those in a conventional optical disk apparatus. Therefore, further details will be omitted.

The foreign body detection circuit 150 corresponds to the foreign body detection signal generation unit 201 and the foreign body discrimination signal generation unit 203 shown in FIG. 25. The operation control circuit 122 includes the function of the control unit 205 shown in FIG. 25. The process execution unit 136 executes a predetermined process upon the detection of a foreign body, and includes a notification unit 136a, a cleaning mechanism 136b, and a disk loading/unloading mechanism 136c. Further, the process execution unit 136 corresponds to the process execution unit 207 shown in FIG. 25.

In FIG. 26, when a foreign body on an optical disk surface is to be detected, control signals S2 and S3 are output from the operation control circuit 122. The control signal S2 is input to the tracking control circuit 120a. The tracking control circuit 120a stops the tracking control operation based on the control signal S2 to stop a tracing operation of the object lens 110 on the information track of the optical disk 100. In this stop state, the action of the tracking actuator 113 is stopped to set the state shown in FIG. 4. The tracking actuator 113 may be vibrated by the control signal S2, so that the light spot 11 may be vibrated at a desired amplitude in the radial direction of the object lens 110 as shown in FIG. 5. The stoppage of the action of the tracking actuator 113 or the vibration of the tracking actuator 113 is selectively used depending on a target.

The control signal S3 is input to the focus drive control circuit 120. The focus drive control circuit 120 switches focal points based on the control signal S3 such that the light spot 11 is focused on the surface of the optical disk 100. In addition, the optical head moving mechanism, as shown in FIGS. 4 and 5, moves the optical head at a predetermined rate such that the locus of the light spot 11 is spiral on the surface of the optical disk 100. At this time, a spindle motor 116 rotates the optical disk 100. The rotating speed of the spindle motor 116 is set such that relative speed of the light spot 11 focused on the surface of the optical disk 100 and the optical disk falls within the range of 1 m/s to 100 m/s. In general, foreign body detection is performed before a recording operation or reproducing operation to or from the optical disk 100.

Figure 28:
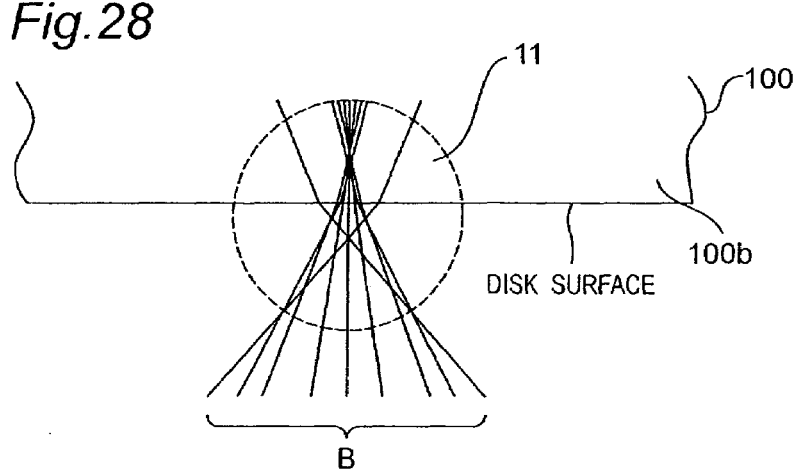
FIG. 28 is a diagram showing an appearance of a light spot on the surface of an optical disk.

FIG. 28 shows the beam of the light spot 11 in FIG. 27A by a ray tracking method. When the light spot 11 is focused on the surface of the optical disk 100, a spherical aberration is generated. An off-axis ray as an outer beam is focused before the disk surface, and a paraxial ray as an inner beam is focused in the disk. More specifically, due to the generation of spherical aberration, the diameter of a spot focused on the disk surface is larger than the diameter of the light spot focused on the information recording layer 100a which is an in-focus position in a recording/reproducing operation. Furthermore, due to the generation of spherical aberration, when the light spot is focused on the disk surface, the wavefronts of the laser beam are not equal to each other. The laser beam is suitable for foreign body detection. With respect to a detection operation of a foreign body adhering to the surface of the optical disk 100 of the optical disk apparatus, an embodiment using a band-pass filter will be described below.

A photodetection signal HF output from the surface of the optical disk 100 is input to the foreign body detection circuit 150 to determine the presence/absence of a foreign body. At this time, when the foreign body detection circuit 150 generates a foreign body detection signal by using a band-pass filter shown in FIG. 11, the passing frequency band of the band-pass filter is preferably set to fall within the range of 10 Hz to 100 KHz. In addition, a foreign body detection signal is generated by using the high-pass filter shown in FIG. 20, where the cutoff frequency of the high-pass filter is preferably set to fall within the range of 0.1 MHz to 100 MHz. With such settings, a foreign body having a size of 1 µm or less can be detected.

The foreign body discrimination signal output from the foreign body detection circuit 150 is input to the operation control circuit 122. When a foreign body is detected, the operation control circuit 122 outputs a control signal to the process execution unit 136 such that a predetermined process upon the detection of a foreign body is performed.

For example, the operation control circuit 122 outputs a control signal for warning by video, voice, or the like to the notification unit 136a. The notification unit 136a outputs a video, voice, or the like in response to the control signal. Alternatively, the operation control circuit 122 outputs a control signal to the cleaning mechanism 136b to instruct a cleaning operation for removing the foreign body from the disk surface. Alternatively, the operation control circuit 122 outputs a control signal to the disk loading/unloading mechanism 136c to instruct the disk loading/unloading mechanism 136c to unload the optical disk 100. Furthermore, the operation control circuit 122 may output a control signal for instructing the signal processing circuit 125 to stop a recording or reproducing operation or a control signal for instructing the signal processing circuit 125 to perform a recording or reproducing operation to a portion except for a region on the optical disk 100 in which a foreign body is detected, to the signal processing circuit 125. The above processes are set as needed.

The foreign body detection for the optical disk 100 is performed when the optical disk apparatus is powered on or when the optical disk 100 is inserted into the optical disk apparatus, i.e., before a recording operation or a reproducing operation is executed. The foreign body detection circuit 150 is preferably operated in a standby state for driving a recording operation or a reproducing operation because the device reliability against a foreign body is improved.

When a foreign body detection experiment on the optical disk surface was performed by using this device, a foreign body having a reflectance which is different from that of the optical disk surface by 10% or less or a foreign body such as a fingerprint which transmits light could be detected. A foreign body could be detected even in an environment of −15° C. to 85° C. without depending on a temperature.

In place of convergence of a light spot on an optical disk surface, convergence of a light spot on the information recording layer of an optical disk can also be used. In this case, since the light spot defocuses on the optical disk surface, the light beam spreads more, and a foreign body can be extensively detected.

Eleventh Embodiment

Figure 29:
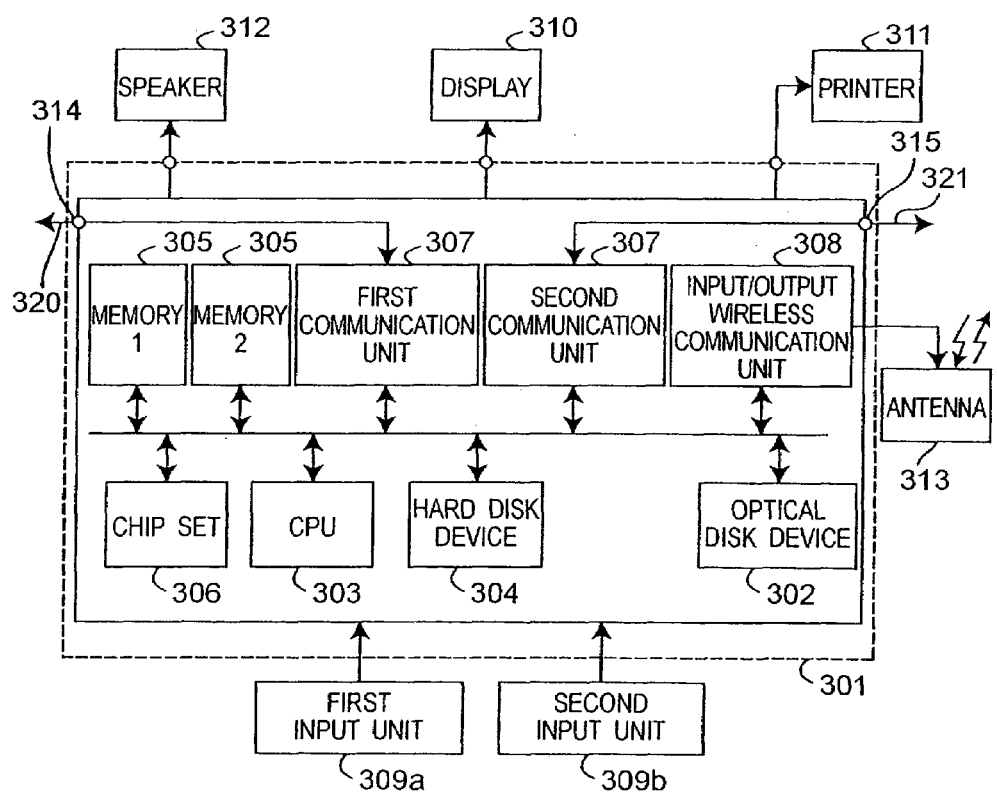
FIG. 29 is a block diagram showing a configuration of a computer system which is equipped with the optical disk apparatus according to the present invention.

FIG. 29 is a block diagram showing a configuration of a computer system which is equipped with the optical disk apparatus according to the present invention. This system includes a computer 301 and peripheral units 309a, 309b, 310, . . . .

The computer 301 includes an optical disk apparatus (device) 302, a CPU 303, a hard disk device 304, a memory 305, a chip set 306, a communication unit 307, an input/output wireless unit 308, connection terminals 314 and 315 connected to the external transmission paths 320 and 321, respectively, and the like.

The peripheral units include input units 309a and 309b such as a keyboard, a mouse, a pen, and a scanner, a display unit 310 such as a liquid crystal display, a printer 311, a loudspeaker 312, and an antenna 313 connected to the input/output wireless unit 308.

The optical disk apparatus 302 has the same configuration and functions as those of the optical disk apparatus described in the ninth and tenth embodiments. Therefore, the optical disk apparatus 302 detects a foreign body adhering to the optical disk surface and can perform cleaning, stoppage of a recording/reproducing operation, or the like for the optical disk upon the detection of a foreign body. This allows the computer according to this embodiment to record and reproduce high-density information on/from an optical disk, and provides improved reliability in a recording/reproducing operation. More specifically, the reliability of the computer system as a whole is advantageously improved.

Twelfth Embodiment

Figure 30:
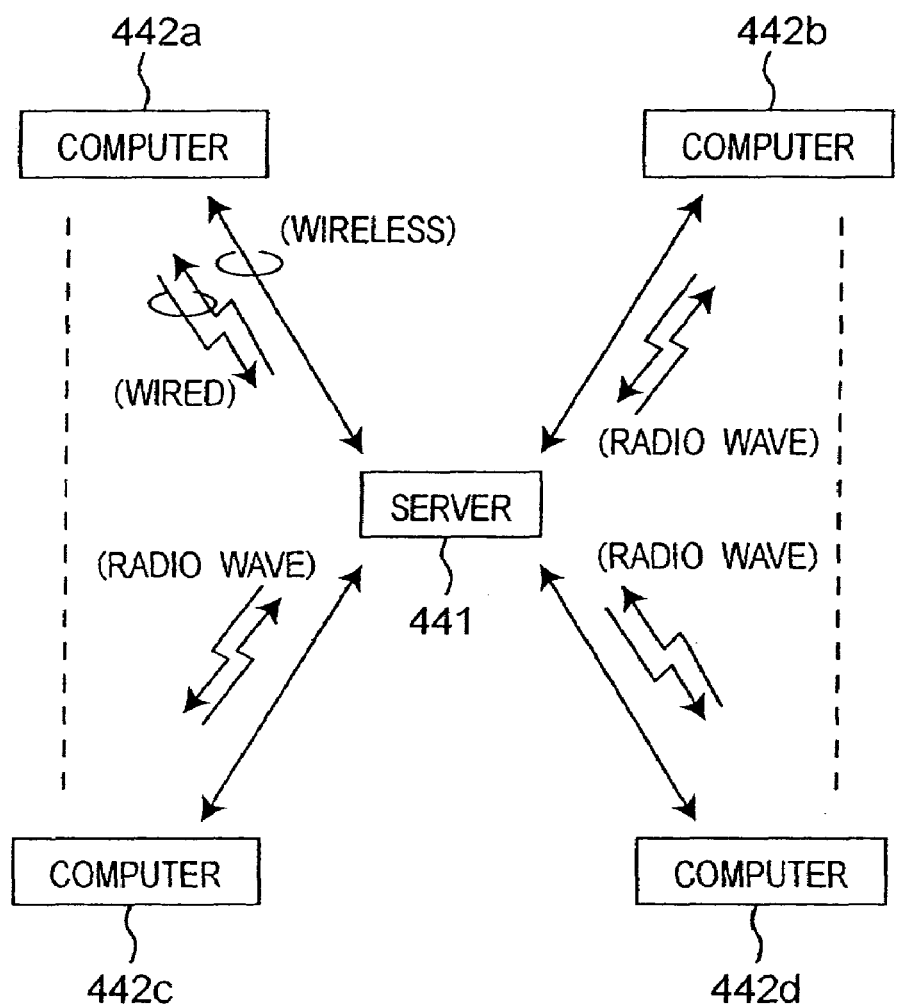
FIG. 30 is a block diagram showing a configuration of a computer network system which is equipped with the optical disk apparatus according to the present invention.

FIG. 30 is a diagram showing a configuration of a network system containing a computer which is equipped with the optical disk apparatus according to the present invention.

This network system includes a server 441 and a plurality of computers 442a to 442d which are connected to each other through a wireless or wired communication medium.

At least one of the computers 442a to 442d has the same configuration as that of the computer described in the eleventh embodiment which is equipped with the optical disk apparatus. In the example shown in FIG. 30, the plurality of optical disk apparatus built-in computers are connected to one server. However, a plurality of servers may be connected. At least one of the optical disk apparatus built-in computers may be connected to the network. The optical disk apparatus described in the eleventh embodiment may be mounted on the server 441. With this configuration, a network system which requires high reliability is improved in reliability.

Thirteenth Embodiment

Figure 31:
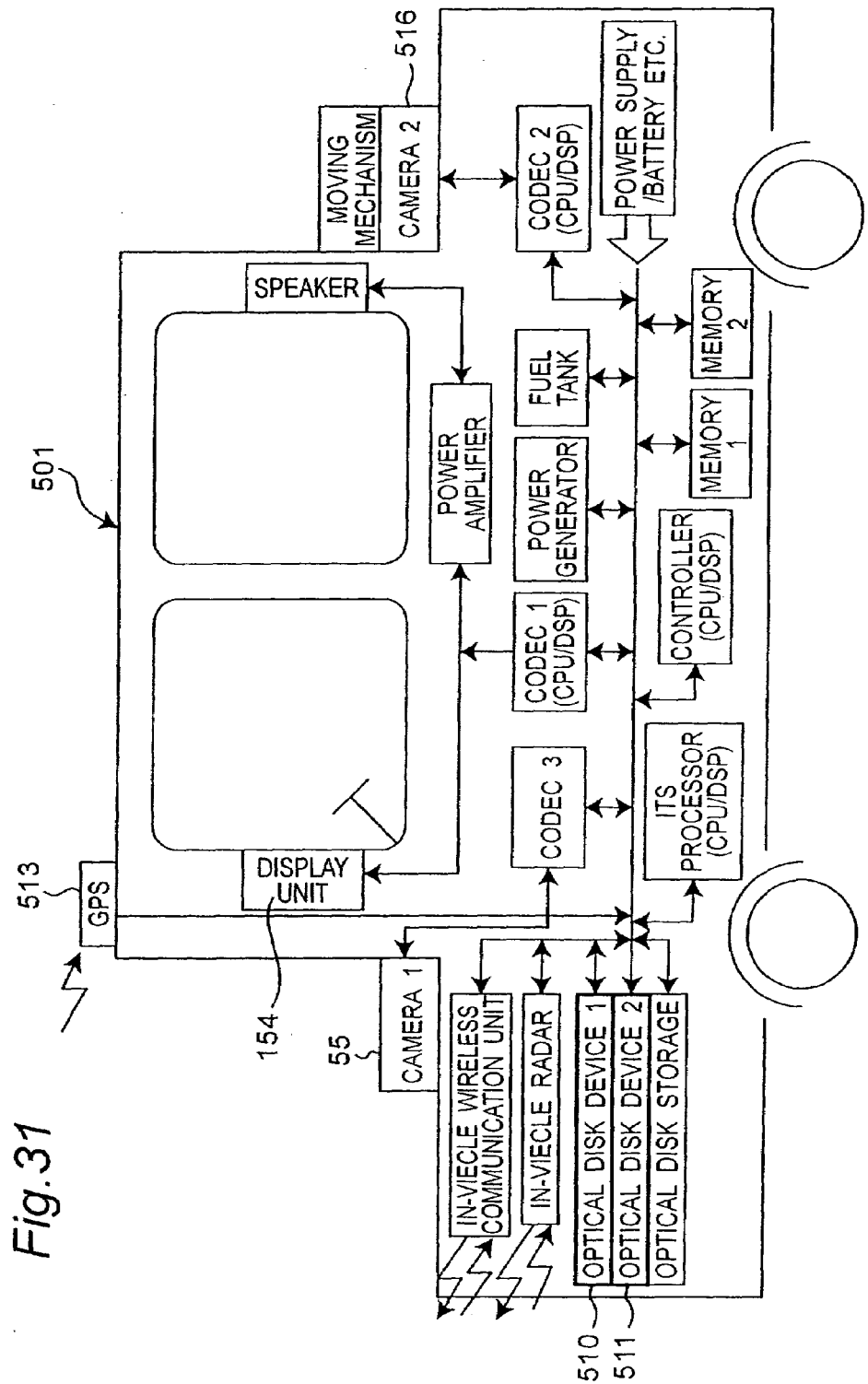
FIG. 31 is a block diagram showing a configuration of an automobile which is equipped with the optical disk apparatus according to the present invention.

FIG. 31 is a block diagram showing a configuration of an automobile which is equipped with the optical disk apparatus according to the present invention. The automobile includes optical disk apparatuses 510 and 511 built in the vehicle body such as in a dashboard or a trunk area. At least one of the optical disk apparatuses 510 and 511 has the same configuration as that of the optical disk apparatus according to the ninth and tenth embodiments.

The optical disk apparatus 510 is a device for reproducing or recording various pieces of information such as a video, a game, and a map, or records these pieces of information from or to the optical disk. It is noted that the applications of the optical disk apparatus 510 are not limited.

The automobile has a car navigation system. The car navigation system includes a GPS (Global Positioning System) 513, the optical disk devices 510 and 511, and a display unit 154 for displaying video signals from the optical disk devices 510 and 511.

According to the automobile equipped with the car navigation system, a foreign body on an optical disk surface can be detected at a high accuracy, a problem can be prevented from being caused by a foreign body, and the reliability of the system can be improved.

Cameras 515 and 516 are mounted at the front and rear of the automobile, and images photographed by the cameras 515 and 516 may be recorded on the optical disks by the optical disk devices 510 and 511. In this manner, for example, images around the automobile are recorded while driving, and these images are reproduced, so that states in driving can be investigated later. In particular, these images are useful for an investigation performed by images and sound obtained when a traffic accident occurs. When these image and sound information are accumulated as a database in another recording device after the accident occurs, an effective measure for the prevention of traffic accidents can be easily achieved.

The automobile is described in this embodiment. However, the optical disk apparatus can be applied to not only an automobile, but also a train, an airplane, a ship, or any other vehicle (transportation) as a matter of course.

Fourteenth Embodiment

An example in which the optical disk apparatus according to the present invention is applied to an image complex machine which integrally achieves functions of a facsimile, a copying machine, a scanner, and a printer.

Figure 32:
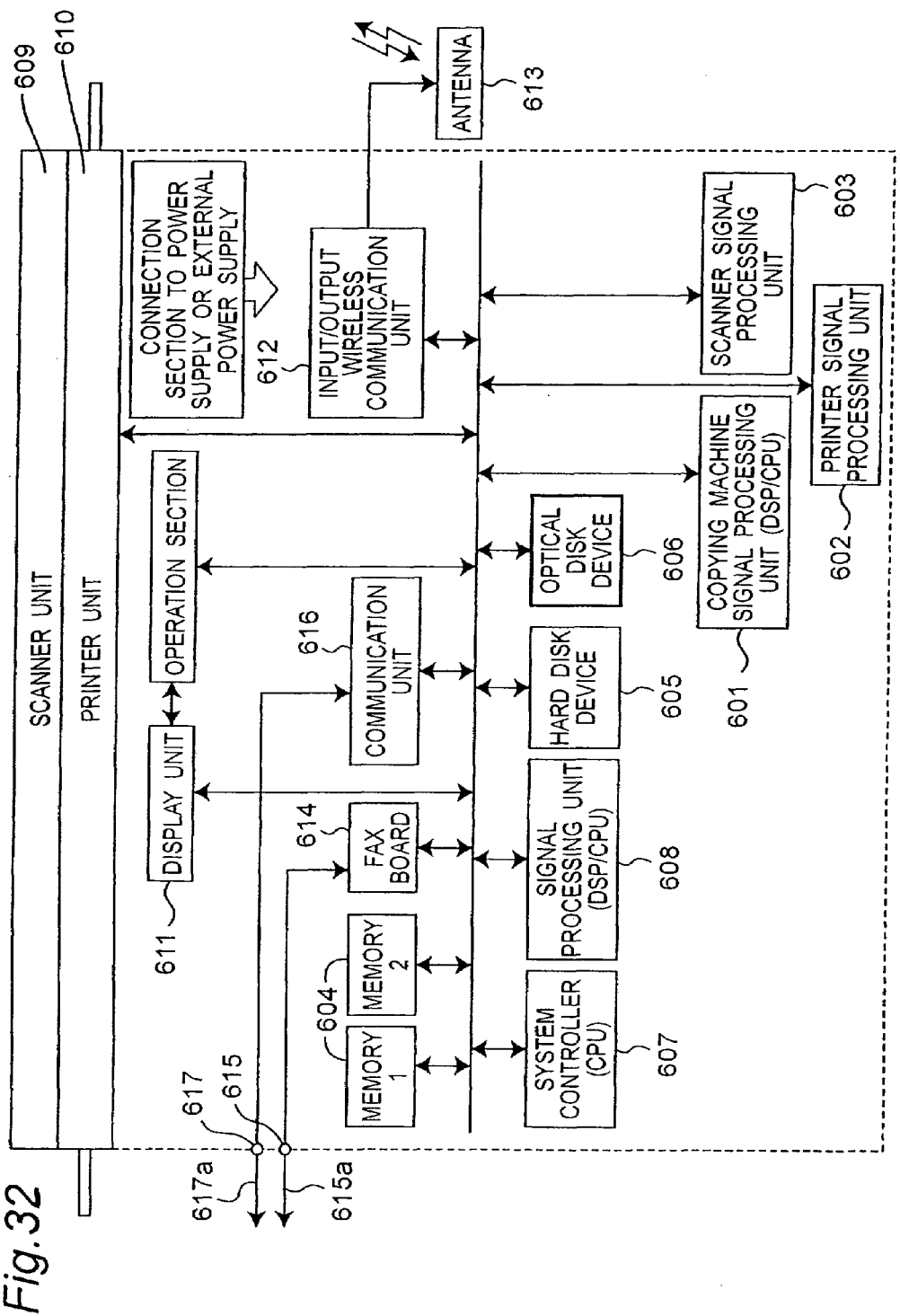
FIG. 32 is a block diagram showing a configuration of an image complex apparatus which is equipped with the optical disk apparatus according to the present invention.

FIG. 32 is a block diagram showing a configuration of an image complex machine which is equipped with the optical disk apparatus according to the present invention.

The image complex machine includes a copying machine signal processing unit 601, a printer signal processing unit 602, a scanner signal processing unit 603, a memory 604, a hard disk device 605, an optical disk apparatus 606, a system controller 607, a signal processing unit 608 (digital signal processor), a scanner unit 609, a printer unit 610, a display unit 611 such as a liquid crystal display, an input/output wireless unit 612, an antenna 613 connected to the input/output wireless unit 612, a facsimile board 614, a connection terminal 615 connected to a telephone circuit 615a, a communication unit 616, and a connection terminal 617 for connecting the communication unit 616 to an external computer through an external transmission path 617a.

The copying machine signal processing unit 601 processes image information, a control signal, or the like when the image complex machine operates as a copying machine. The printer signal processing unit 602 processes image information, a control signal, or the like when the image composite apparatus operates as a printer. The scanner signal processing unit 603 processes image information, a control signal, or the like when the image composite apparatus operates as a scanner.

As the printer unit 610, a printer such as a laser printer or an inkjet printer using any printing method may be used.

The optical disk apparatus 606 is an optical disk apparatus described in the ninth and tenth embodiments. The optical disk apparatus 606 records information transmitted and received by a facsimile, image information scanned in copying, information required to be printed by an external computer, and the like on an optical disk.

In this manner, with the configuration of the optical disk apparatus according to the present invention which is built in the image complex machine, a recording/reproducing operation can be performed without being adversely affected by a foreign body adhering to an optical disk surface, when recording or reproducing facsimile transmission/reception information or the like to or from an optical disk. The reliability of the image complex machine can be improved.

Fifteenth Embodiment

Figure 33:
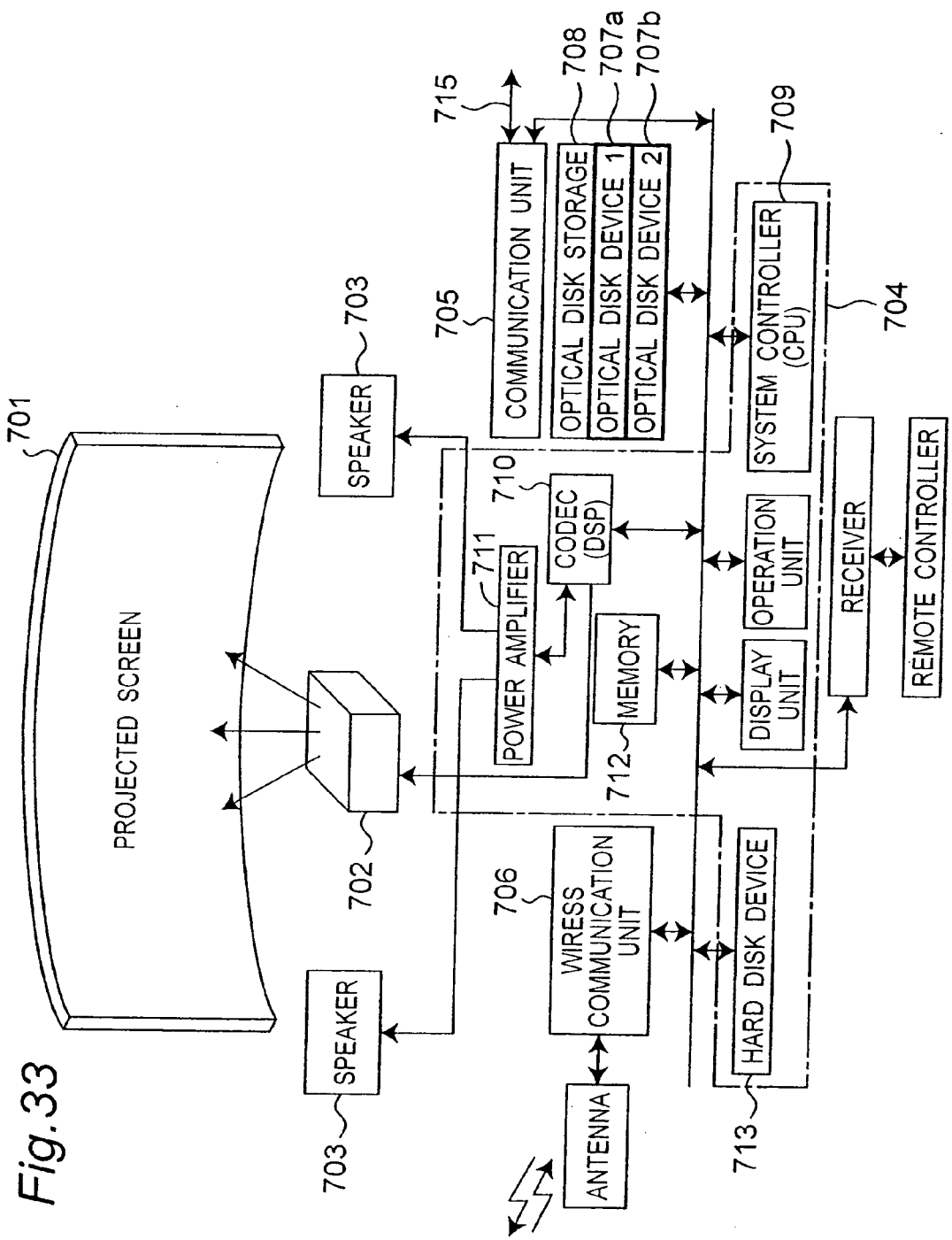
FIG. 33 is a block diagram showing a configuration of a cinema system which is equipped with the optical disk apparatus according to the present invention.
Figure 34:
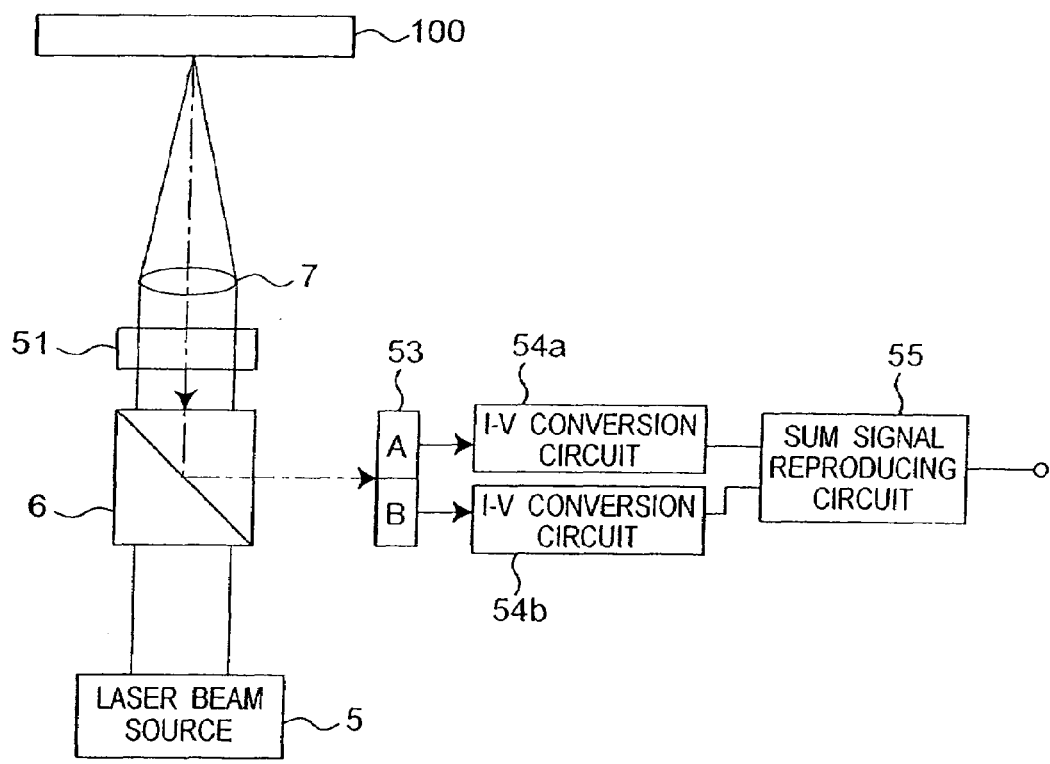
FIG. 34 is a block diagram showing a configuration of a conventional foreign body detection apparatus.

FIG. 33 is a block diagram showing a configuration of a cinema system which is equipped with the optical disk apparatus according to the present invention.

The cinema system includes a projection screen 701, a video projection unit 702 such as a liquid crystal projection unit for projecting a video on the projection screen 701, a loudspeaker 703, a control unit 704 for generating a video/audio signal, a communication unit 705 connected to an external transmission path 715, a wireless communication unit 706 for performing satellite communication or the like, two optical disk apparatuses 707a and 707b, an optical disk storage unit 708 which stores an optical disk loaded on the optical disk apparatuses 707a and 707b, and the like.

The optical disk apparatuses 707a and 707b have the same configurations as those of the optical disk apparatuses described in the ninth and tenth embodiments.

The control unit 704 includes a system controller 709 for performing image processing of a video signal and a control for stopping the optical disk apparatus 707a in a projection operation based on a foreign body discrimination signal output from the optical disk apparatus 707a in order to switch it to the optical disk apparatus 707b, a codec 710, a power amplifier 711, a memory 712, a hard disk 713, and the like. The control unit 704 generates a video signal and an audio signal based on reproduced signals from the optical disk apparatuses 707a and 707b, and controls the operation of the cinema system as a whole.

The cinema system preferably includes two or more optical disk apparatuses. In this case, when the control unit 704 detects a foreign body on an optical disk surface in reproduction of an optical disk, the control unit 704 performs the control so as to stop the optical disk apparatus in reproduction and switch the optical disk apparatus to another optical disk apparatus for reproduction. Thus, screening can be advantageously continued without interrupting projection.

An operation of the system controller 709 which, when detecting a foreign body on an optical disk surface, stops a reproducing operation of the optical disk apparatus 707a in reproduction and switches it to another apparatus 707b to continue a reproducing operation will be described below.

When a foreign body discrimination signal output from the optical disk apparatus 707a is input to the system controller 709, the system controller 709 outputs, to the optical disk apparatus 707a, a signal for instructing the apparatus 707a in reproduction to stop the reproducing operation, and outputs, to the optical disk apparatus 707b, a signal for instructing the apparatus 707b to start the reproducing operation. In this manner, the optical disk apparatus 707a in reproduction is switched to the other optical disk apparatus 707b, and the reproducing operation is continuously performed by the other optical disk apparatus 707b.

Therefore, use of an optical disk built-in cinema system according to the present invention can prevent discontinuity of a reproduced video even though a foreign body adheres to the surface of an optical disk in reproduction. Hence, a long movie recorded on a large-capacity optical disk can be projected in a theater or the like.

The present invention has been described in the specific embodiments, although a large number of other modifications, corrections, and applications are apparent to a person skilled in the art. Therefore, the present invention is not limited to the specific disclosures, and can be limited by only the spirit and scope of claims.

This application is related to Japanese Patent Application No. 2002-156889 (filed on May 30, 2002), Japanese Patent Application No. 2002-195488 (filed on Jul. 4, 2002), Japanese Patent Application No. 2002-227138 (filed on Aug. 5, 2002), Japanese Patent Application No. 2002-265101 (filed on Sep. 11, 2002), and Japanese Patent Application No. 2003-075691 (filed on Mar. 19, 2003), the contents of which are incorporated herein by reference.

The invention claimed is:

1. An apparatus for detecting a foreign body on an object surface, said apparatus comprising:
   an irradiation unit for irradiating a light spot onto a surface of an object to be inspected while scanning the surface by irradiating the light spot in a predetermined direction;
   an optical signal detection unit for receiving a reflected beam from the surface of the inspected object to generate a photodetection signal corresponding to the light intensity of the reflected beam;
   a foreign body detection unit for generating a foreign body detection signal appearing with respect to a leader and a trailer in the scanning direction of a foreign body adhering to the inspected object, based on the photodetection signal; and
   a foreign body discrimination unit for generating a foreign body discriminating signal indicating a region in which the foreign body is present based on the foreign body detection signal,
   wherein said foreign body discrimination unit includes a first comparison unit for comparing the output from said foreign body detection unit with a first reference voltage, and a second comparison unit for comparing the output from said foreign body detection unit with a second reference voltage, and
   wherein said foreign body discrimination unit further includes an RS flipflop circuit for inputting the respective output signals from said first and second comparison units.

2. An apparatus for detecting a foreign body on an object surface, said apparatus comprising:
   an irradiation unit for irradiating a light spot onto a surface of an object to be inspected while scanning the surface by irradiating the light spot in a predetermined direction;
   an optical signal detection unit for receiving a reflected beam from the surface of the inspected object to generate a photodetection signal corresponding to the light intensity of the reflected beam;
   a foreign body detection unit for generating a foreign body detection signal appearing with respect to a leader and a trailer in the scanning direction of a foreign body adhering to the inspected object, based on the photodetection signal; and
   a foreign body discrimination unit for generating a foreign body discriminating signal indicating a region in which the foreign body is present based on the foreign body detection signal,
   wherein said foreign body discrimination unit includes a first comparison unit for comparing the output from said foreign body detection unit with a first reference voltage, and a second comparison unit for comparing the output from said foreign body detection unit with a second reference voltage, and
   wherein the reference voltages of said first and second comparison units are set at an average value of voltages corresponding to light intensities of reflected beams from the surface of the inspected object to which a foreign body does not adhere.

3. An apparatus for detecting a foreign body on an object surface, said apparatus comprising:
   an irradiation unit for irradiating a light spot onto a surface of an object to be inspected while scanning the surface by irradiating the light spot in a predetermined direction;
   an optical signal detection unit for receiving a reflected beam from the surface of the inspected object to generate a photodetection signal corresponding to the light intensity of the reflected beam;
   a foreign body detection unit for generating a foreign body detection signal appearing with respect to a leader and a trailer in the scanning direction of a foreign body adhering to the inspected object, based on the photodetection signal; and
   a foreign body discrimination unit for generating a foreign body discriminating signal indicating a region in which the foreign body is present based on the foreign body detection signal,
   wherein said foreign body discrimination unit includes a first comparison unit for comparing the output from said foreign body detection unit with a first reference voltage, and a second comparison unit for comparing the output from said foreign body detection unit with a second reference voltage, and
   wherein the reference voltages of the comparison units are reset each time the detection of a foreign body is started.

4. An apparatus for detecting a foreign body on an object surface, said apparatus comprising:
   an irradiation unit for irradiating a light spot onto a surface of an object to be inspected while scanning the surface by irradiating the light spot in a predetermined direction;
   an optical signal detection unit for receiving a reflected beam from the surface of the inspected object to generate a photodetection signal corresponding to the light intensity of the reflected beam;
   a foreign body detection unit for generating a foreign body detection signal appearing with respect to a leader and a trailer in the scanning direction of a foreign body adhering to the inspected object, based on the photodetection signal; and a foreign body discrimination unit for generating a foreign body discriminating signal indicating a region in which the foreign body is present based on the foreign body detection signal, wherein when the inspected object has a disk-like shape, said irradiation unit is operable to irradiate the light spot to scan the object to be inspected such that the locus of the light spot is spiral from the center of the inspected object, and wherein said irradiation unit is operable to irradiate the light spot to scan the inspected object while the light spot is vibrated at a predetermined amplitude such that the center locus of the amplitude traces the spiral locus.

5. An apparatus for detecting a foreign body on an object surface, said apparatus comprising:

an irradiation unit for irradiating a light spot onto a surface of an object to be inspected while scanning the surface by irradiating the light spot in a predetermined direction;

an optical signal detection unit for receiving a reflected beam from the surface of the inspected object to generate a photodetection signal corresponding to the light intensity of the reflected beam;

a foreign body detection unit for generating a foreign body detection signal appearing with respect to a leader and a trailer in the scanning direction of a foreign body adhering to the inspected object, based on the photodetection signal; and a foreign body discrimination unit for generating a foreign body discriminating signal indicating a region in which the foreign body is present based on the foreign body detection signal, wherein said foreign body detection unit includes a band-pass filter for causing the photodetection signal to pass therethrough to generate a band-pass signal, and said foreign body discrimination unit is operable to generate the foreign body discrimination signal based on the band-pass signal, and wherein, when the inspected object has a disk-like shape, and when said irradiation unit irradiates the light spot to scan the inspected object while the inspected object is rotated at a linear velocity of 1 to 100 m/s, the passing frequency band of said band-pass filter falls within a range of 10 Hz to 100 kHz.

6. An optical disk apparatus for irradiating a laser beam on an optical disk to record or reproduce information, said optical disk apparatus comprising:

a foreign body detection apparatus for detecting a foreign body adhering to the surface of an optical disk which is an object to be inspected, wherein said foreign body detection apparatus comprises:

an irradiation unit for irradiating a light spot onto a surface of an object to be inspected while scanning the surface by irradiating the light spot in a predetermined direction;

an optical signal detection unit for receiving a reflected beam from the surface of the inspected object to generate a photodetection signal corresponding to the light intensity of the reflected beam;

a foreign body detection unit for generating a foreign body detection signal appearing with respect to a leader and a trailer in the scanning direction of a foreign body adhering to the inspected object, based on the photodetection signal; and a foreign body discrimination unit for generating a foreign body discriminating signal indicating a region in which the foreign body is present based on the foreign body detection signal, and wherein the optical disk is a phase-change type optical recording medium, and the thickness of light-transmitting layer falls within a range of 0.01 to 1200 μm.

7. An optical disk apparatus for irradiating a laser beam on an optical disk to record or reproduce information, said optical disk apparatus comprising:

a foreign body detection apparatus for detecting a foreign body adhering to the surface of an optical disk which is an object to be inspected, wherein said foreign body detection apparatus comprises:

an irradiation unit for irradiating a light spot onto a surface of an object to be inspected while scanning the surface by irradiating the light spot in a predetermined direction;

an optical signal detection unit for receiving a reflected beam from the surface of the inspected object to generate a photodetection signal corresponding to the light intensity of the reflected beam;

a foreign body detection unit for generating a foreign body detection signal appearing with respect to a leader and a trailer in the scanning direction of a foreign body adhering to the inspected object, based on the photodetection signal; and a foreign body discrimination unit for generating a foreign body discriminating signal indicating a region in which the foreign body is present based on the foreign body detection signal, and wherein said foreign body detection apparatus is operable to execute a foreign body detecting operation during a standby state for driving the recording or reproducing operation.

8. A method of detecting a foreign body on a surface of an object, said method comprising:

irradiating a light spot onto a surface of an object to be inspected while scanning the surface by irradiating the light spot in a predetermined direction;

receiving a reflected beam from the surface of the inspected object to generate a photodetection signal corresponding to the light intensity of the reflected beam;

generating a foreign body detection signal appearing with respect to a leader and a trailer in the scanning direction of the foreign body adhering to the inspected object, based on the photodetection signal; and generating a foreign body discriminating signal indicating a region in which the foreign body is present based on the foreign body detection signal, wherein:

said generating of the foreign body detection signal includes causing the photodetection signal to pass through a band-pass filter to generate a band-pass signal, and said generating of the foreign body discrimination signal includes generating the foreign body discrimination signal based on the band-pass signal; and the band pass filter includes a first low-pass filter and a second low-pass filter.

9. The detecting method according to claim 8, wherein the first and second low-pass filters are serially connected.

10. An apparatus for detecting a foreign body on an object surface, said apparatus comprising:

an irradiation unit for irradiating a light spot onto a surface of an object to be inspected while scanning the surface by irradiating the light spot in a predetermined direction;

an optical signal detection unit for receiving a reflected beam from the surface of the inspected object to generate a photodetection signal corresponding to the light intensity of the reflected beam;

a foreign body detection unit for generating a foreign body detection signal appearing with respect to a leader and a trailer in the scanning direction of a foreign body adhering to the inspected object, based on the photodetection signal; and a foreign body discrimination unit for generating a foreign body discriminating signal indicating a region in which the foreign body is present based on the foreign body detection signal, wherein said foreign body detection unit includes a band-pass filter for causing the photodetection signal to pass therethrough to generate a band-pass signal, and said foreign body discrimination unit is operable to generate the foreign body discrimination signal based on the band-pass signal; and wherein said band pass filter includes a first low-pass filter and a second low-pass filter.

11. The detecting apparatus according to claim 10, wherein said first and second low-pass filters are serially connected.

12. The detecting apparatus according to claim 1, wherein said foreign body detection unit comprises a delay unit for generating a delay signal obtained by delaying the photodetection signal by a predetermined time, and a subtraction unit for generating a difference signal as the foreign body detection signal by performing subtraction between the delay signal and the photodetection signal.

13. The detecting apparatus according to claim 1, wherein said foreign body detection unit comprises:

a first delay unit for generating a first delay signal obtained by delaying the photodetection signal by a first delay time;

a second delay unit for generating a second delay signal obtained by delaying the photodetection signal by a second delay time; and a subtraction unit for performing subtraction between the first delay signal and the second delay signal to generate a difference signal as the foreign body detection signal.

14. The detecting apparatus according to claim 1, wherein said foreign body detection unit comprises a low-pass filter for causing the photodetection signal to pass therethrough to generate a low-band signal, and a subtraction unit for performing subtraction between the photodetection signal and the low-band signal to generate a difference signal as the foreign body detection signal.

15. The detecting apparatus according to claim 1, wherein said foreign body detection unit comprises:

a first low-pass filter for causing the photodetection signal to pass therethrough to generate a first low-band signal;

a second low-pass filter, which has a passing band characteristic different from that of said first low-pass filter, for causing the photodetection signal to pass therethrough to generate a second low-band signal; and a subtraction unit for performing subtraction between the first low-band signal and the second low-band signal to generate a difference signal as the foreign body detection signal.

16. The detecting apparatus according to claim 1, wherein said foreign body detection unit comprises:

a first low-pass filter for causing low-band components of the photodetection signal to pass therethrough to generate a first low-band signal;

a second low-pass filter, which has a passing band characteristic different from that of said first low-pass filter, for causing the first low-band signal to pass therethrough to generate a second low-band signal; and a subtraction unit for performing subtraction between the first low-band signal and the second low-band signal to generate a difference signal as the foreign body detection signal.

17. The detecting apparatus according to claim 1, wherein said foreign body detection unit comprises a high-pass filter for causing the photodetection signal to pass therethrough to generate a high-band signal as the foreign body detection signal.

18. The detecting apparatus according to claim 17, wherein, when the inspected object has a disk-like shape and said irradiation unit irradiates the light spot to scan the inspected object while the inspected object is rotated at a linear velocity of 1 to 100 m/s, the cutoff frequency of said high-pass filter is set within a range of 0.1 MHz to 100 MHz.

19. The detecting apparatus according to claim 2, wherein said foreign body detection unit comprises a delay unit for generating a delay signal obtained by delaying the photodetection signal by a predetermined time, and a subtraction unit for generating a difference signal as the foreign body detection signal by performing subtraction between the delay signal and the photodetection signal.

20. The detecting apparatus according to claim 2, wherein said foreign body detection unit comprises:

a first delay unit for generating a first delay signal obtained by delaying the photodetection signal by a first delay time;

a second delay unit for generating a second delay signal obtained by delaying the photodetection signal by a second delay time; and a subtraction unit for performing subtraction between the first delay signal and the second delay signal to generate a difference signal as the foreign body detection signal.

21. The detecting apparatus according to claim 2, wherein said foreign body detection unit comprises a low-pass filter for causing the photodetection signal to pass therethrough to generate a low-band signal, and a subtraction unit for performing subtraction between the photodetection signal and the low-band signal to generate a difference signal as the foreign body detection signal.

22. The detecting apparatus according to claim 2, wherein said foreign body detection unit comprises:

a first low-pass filter for causing the photodetection signal to pass therethrough to generate a first low-band signal;

a second low-pass filter, which has a passing band characteristic different from that of said first low-pass filter, for causing the photodetection signal to pass therethrough to generate a second low-band signal; and a subtraction unit for performing subtraction between the first low-band signal and the second low-band signal to generate a difference signal as the foreign body detection signal.

23. The detecting apparatus according to claim 2, wherein said foreign body detection unit comprises:

a first low-pass filter for causing low-band components of the photodetection signal to pass therethrough to generate a first low-band signal;

a second low-pass filter, which has a passing band characteristic different from that of said first low-pass filter, for causing the first low-band signal to pass therethrough to generate a second low-band signal; and a subtraction unit for performing subtraction between the first low-band signal and the second low-band signal to generate a difference signal as the foreign body detection signal.

24. The detecting apparatus according to claim 2, wherein said foreign body detection unit comprises a high-pass filter for causing the photodetection signal to pass therethrough to generate a high-band signal as the foreign body detection signal.

25. The detecting apparatus according to claim 24, wherein, when the inspected object has a disk-like shape and said irradiation unit irradiates the light spot to scan the inspected object while the inspected object is rotated at a linear velocity of 1 to 100 m/s, the cutoff frequency of said high-pass filter is set within a range of 0.1 MHz to 100 MHz.

26. The detecting apparatus according to claim 3, wherein said foreign body detection unit comprises a delay unit for generating a delay signal obtained by delaying the photodetection signal by a predetermined time, and a subtraction unit for generating a difference signal as the foreign body detection signal by performing subtraction between the delay signal and the photodetection signal.

27. The detecting apparatus according to claim 3, wherein said foreign body detection unit comprises:
   a first delay unit for generating a first delay signal obtained by delaying the photodetection signal by a first delay time;
   a second delay unit for generating a second delay signal obtained by delaying the photodetection signal by a second delay time; and
   a subtraction unit for performing subtraction between the first delay signal and the second delay signal to generate a difference signal as the foreign body detection signal.

28. The detecting apparatus according to claim 3, wherein said foreign body detection unit comprises a low-pass filter for causing the photodetection signal to pass therethrough to generate a low-band signal, and a subtraction unit for performing subtraction between the photodetection signal and the low-band signal to generate a difference signal as the foreign body detection signal.

29. The detecting apparatus according to claim 3, wherein said foreign body detection unit comprises:
   a first low-pass filter for causing the photodetection signal to pass therethrough to generate a first low-band signal;
   a second low-pass filter, which has a passing band characteristic different from that of said first low-pass filter, for causing the photodetection signal to pass therethrough to generate a second low-band signal; and
   a subtraction unit for performing subtraction between the first low-band signal and the second low-band signal to generate a difference signal as the foreign body detection signal.

30. The detecting apparatus according to claim 3, wherein said foreign body detection unit comprises:
   a first low-pass filter for causing low-band components of the photodetection signal to pass therethrough to generate a first low-band signal;
   a second low-pass filter, which has a passing band characteristic different from that of said first low-pass filter, for causing the first low-band signal to pass therethrough to generate a second low-band signal; and
   a subtraction unit for performing subtraction between the first low-band signal and the second low-band signal to generate a difference signal as the foreign body detection signal.

31. The detecting apparatus according to claim 3, wherein said foreign body detection unit comprises a high-pass filter for causing the photodetection signal to pass therethrough to generate the foreign body detection signal a high-band signal as the foreign body detection signal.

32. The detecting apparatus according to claim 31, wherein, when the inspected object has a disk-like shape and said irradiation unit irradiates the light spot to scan the inspected object while the inspected object is rotated at a linear velocity of 1 to 100 m/s, the cutoff frequency of said high-pass filter is set within a range of 0.1 MHz to 100 MHz.

33. The detecting apparatus according to claim 4, wherein said foreign body detection unit comprises a delay unit for generating a delay signal obtained by delaying the photodetection signal by a predetermined time, and a subtraction unit for generating a difference signal as the foreign body detection signal by performing subtraction between the delay signal and the photodetection signal.

34. The detecting apparatus according to claim 4, wherein said foreign body detection unit comprises:
   a first delay unit for generating a first delay signal obtained by delaying the photodetection signal by a first delay time;
   a second delay unit for generating a second delay signal obtained by delaying the photodetection signal by a second delay time; and
   a subtraction unit for performing subtraction between the first delay signal and the second delay signal to generate a difference signal as the foreign body detection signal.

35. The detecting apparatus according to claim 4, wherein said foreign body detection unit comprises a low-pass filter for causing the photodetection signal to pass therethrough to generate a low-band signal, and a subtraction unit for performing subtraction between the photodetection signal and the low-band signal to generate a difference signal as the foreign body detection signal.

36. The detecting apparatus according to claim 4, wherein said foreign body detection unit comprises:
   a first low-pass filter for causing the photodetection signal to pass therethrough to generate a first low-band signal;
   a second low-pass filter, which has a passing band characteristic different from that of said first low-pass filter, for causing the photodetection signal to pass therethrough to generate a second low-band signal; and
   a subtraction unit for performing subtraction between the first low-band signal and the second low-band signal to generate a difference signal as the foreign body detection signal.

37. The detecting apparatus according to claim 4, wherein said foreign body detection unit comprises:
   a first low-pass filter for causing low-band components of the photodetection signal to pass therethrough to generate a first low-band signal;
   a second low-pass filter, which has a passing band characteristic different from that of said first low-pass filter, for causing the first low-band signal to pass therethrough to generate a second low-band signal; and
   a subtraction unit for performing subtraction between the first low-band signal and the second low-band signal to generate a difference signal as the foreign body detection signal.

38. The detecting apparatus according to claim 4, wherein said foreign body detection unit comprises a high-pass filter for causing the photodetection signal to pass therethrough to generate the foreign body detection signal a high-band signal as the foreign body detection signal.

39. The detecting apparatus according to claim 38, wherein, when the inspected object has a disk-like shape and said irradiation unit irradiates the light spot to scan the inspected object while the inspected object is rotated at a linear velocity of 1 to 100 m/s, the cutoff frequency of said high-pass filter is set within a range of 0.1 MHz to 100 MHz.

* * * * *